(12) United States Patent
Appel et al.

(10) Patent No.: US 8,236,349 B2
(45) Date of Patent: Aug. 7, 2012

(54) TASTE-MASKED DRUGS IN RUPTURING MULTIPARTICULATES

(75) Inventors: Leah Elizabeth Appel, Bend, OR (US); Dwayne Thomas Friesen, Bend, OR (US); Edward Dennis LaChapelle, Bend, OR (US); Sanjay Konagurthu, Bend, OR (US); Richard Frank Falk, Bend, OR (US); Joseph P. Reo, Lakeland, TN (US)

(73) Assignee: Bend Research Inc., Bend, OR (US)

( * ) Notice: Subject to any disclaimer, the term of this patent is extended or adjusted under 35 U.S.C. 154(b) by 1388 days.

(21) Appl. No.: 10/599,840

(22) PCT Filed: Apr. 6, 2005

(86) PCT No.: PCT/IB2005/000917
§ 371 (c)(1),
(2), (4) Date: Nov. 17, 2006

(87) PCT Pub. No.: WO2005/097064
PCT Pub. Date: Oct. 20, 2005

(65) Prior Publication Data
US 2007/0196483 A1    Aug. 23, 2007

Related U.S. Application Data

(60) Provisional application No. 60/561,595, filed on Apr. 12, 2004.

(51) Int. Cl.
*A61K 9/26*   (2006.01)
(52) U.S. Cl. ........................................ 424/469
(58) Field of Classification Search .................... None
See application file for complete search history.

(56) References Cited

U.S. PATENT DOCUMENTS

| | | | |
|---|---|---|---|
| 4,871,549 A | 10/1989 | Ueda et al. | 424/480 |
| 4,897,270 A | 1/1990 | Deutsch et al. | 424/465 |
| 5,082,669 A | 1/1992 | Shirai et al. | 424/495 |
| 5,190,760 A | 3/1993 | Baker | 424/438 |
| 5,229,135 A | 7/1993 | Philippon et al. | 424/494 |
| 5,270,055 A | 12/1993 | Moest | 424/476 |
| 5,336,433 A | 8/1994 | Lagnemo et al. | 252/186.23 |
| 5,376,384 A | 12/1994 | Eichel et al. | 424/480 |
| 5,478,573 A | 12/1995 | Eichel et al. | 424/480 |
| 5,536,507 A | 7/1996 | Abramowitz et al. | 424/479 |
| 5,580,578 A | 12/1996 | Oshlack et al. | 424/468 |

(Continued)

FOREIGN PATENT DOCUMENTS

CA    2229650    8/2006

(Continued)

OTHER PUBLICATIONS

The erythromycin MSDS document, accessed Mar. 2011.*

(Continued)

*Primary Examiner* — Paul Dickinson
(74) *Attorney, Agent, or Firm* — Chernoff, Vilhauer, McClung & Stenzel, LLP

(57) ABSTRACT

A pharmaceutical composition comprises multiparticulates comprising a drug, a matrix material, and swelling agent. In one aspect, the multiparticulates comprise a core comprising a drug, and a coating surrounding the core. The coating is selected from the group consisting of (i) a water-permeable, substantially drug-impermeable coating, and (ii) an anti-enteric coating.

14 Claims, 6 Drawing Sheets

U.S. PATENT DOCUMENTS

| | | | |
|---|---|---|---|
| 5,593,690 A | 1/1997 | Akiyama et al. | 424/457 |
| 5,607,697 A | 3/1997 | Alkire et al. | 424/495 |
| 5,639,476 A | 6/1997 | Oshlack et al. | 424/468 |
| 5,656,291 A | 8/1997 | Olsson et al. | 424/458 |
| 5,733,575 A | 3/1998 | Mehra et al. | 424/480 |
| 5,834,024 A | 11/1998 | Heinicke et al. | 424/497 |
| 5,840,329 A * | 11/1998 | Bai | 424/458 |
| 5,914,134 A | 6/1999 | Sharma | 424/497 |
| 5,952,005 A | 9/1999 | Olsson et al. | 424/458 |
| 6,013,282 A | 1/2000 | Mehra et al. | 424/480 |
| 6,027,748 A | 2/2000 | Conte et al. | 424/458 |
| 6,033,687 A | 3/2000 | Heinicke et al. | 424/497 |
| 6,039,976 A | 3/2000 | Mehra et al. | 424/480 |
| 6,077,544 A | 6/2000 | Debregeas et al. | 424/497 |
| 6,086,920 A | 7/2000 | Frisbee et al. | 424/489 |
| 6,117,452 A | 9/2000 | Ahlgren et al. | 424/468 |
| 6,194,000 B1 | 2/2001 | Smith et al. | 424/458 |
| 6,214,385 B1 | 4/2001 | Heinicke et al. | 424/497 |
| 6,228,400 B1 | 5/2001 | Lee et al. | 424/489 US |
| 6,270,805 B1 | 8/2001 | Chen et al. | 424/497 |
| 6,346,269 B1 | 2/2002 | Hsiao et al. | 424/472 |
| 6,723,358 B1 | 4/2004 | Van Lengerich et al. | 426/94 |
| 2001/0055619 A1 | 12/2001 | Petereit et al. | 424/490 |
| 2002/0068084 A1 | 6/2002 | Staniforth | 424/499 |
| 2003/0099700 A1 | 5/2003 | Faham et al. | 424/465 |
| 2004/0026546 A1 * | 2/2004 | Czekai et al. | 241/172 |
| 2005/0123627 A1 * | 6/2005 | Hagen et al. | 424/683 |
| 2006/0127478 A1 * | 6/2006 | Zerbe et al. | 424/472 |

FOREIGN PATENT DOCUMENTS

| | | |
|---|---|---|
| EP | 0169105 | 8/1991 |
| EP | 0309051 | 3/1992 |
| EP | 0409254 | 3/1993 |
| EP | 0523847 | 4/1996 |
| EP | 0737473 | 10/1996 |
| EP | 0494972 | 11/1996 |
| WO | WO 9401093 | 1/1994 |
| WO | WO 9503765 | 2/1995 |
| WO | WO 9503785 | 2/1995 |
| WO | WO 0152813 | 7/2001 |
| WO | WO 0103698 | 11/2001 |
| WO | WO 0180826 | 11/2001 |

OTHER PUBLICATIONS

The carnauba wax JECFA document, accessed Mar. 2011.*
The azithromycin MSDS document, accessed Mar. 2011.*
CA 2, 229,650 equivalent to EP 0 864 326.
Shirai, Y., et al., "*A Novel Fine Granule System for Masking Bitter Taste*", Biol. Pharm. Bull., 1993, pp. 172-177, vol. 16, No. 2.
Sun, Y., et al., "*Pharmaceutical Approaches of Taste Masking in Solid Dosage Forms*", American Pharmaceutical Review, (year unknown), pp. 16-28.
Fan, Y.Y., et al., "*An investigation of Pulsatile Release Tablets with Ethylcellulose and Eudragit L as Film Coating Materials and Cross-Liked Polyvinylpyrrolidone in the Core Tablets*", Journal of Controlled Release, 2001, pp. 245-251, vol. 77.
Reo, J.P., et al., "*Taste Masking Science and Technology Applied to Compacted Oral Solid Dosage Forms-Part 3*", American Pharmaceutical Review, 2002, pp. 8-13, vol. 5, No. 2.
Reo, J.P., et al., "Taste Masking Science and Technology Applied to Compacted Oral Solid Dosage Forms—Part 2", American Pharmaceutical Review, 2006, pp. 8-20.

* cited by examiner

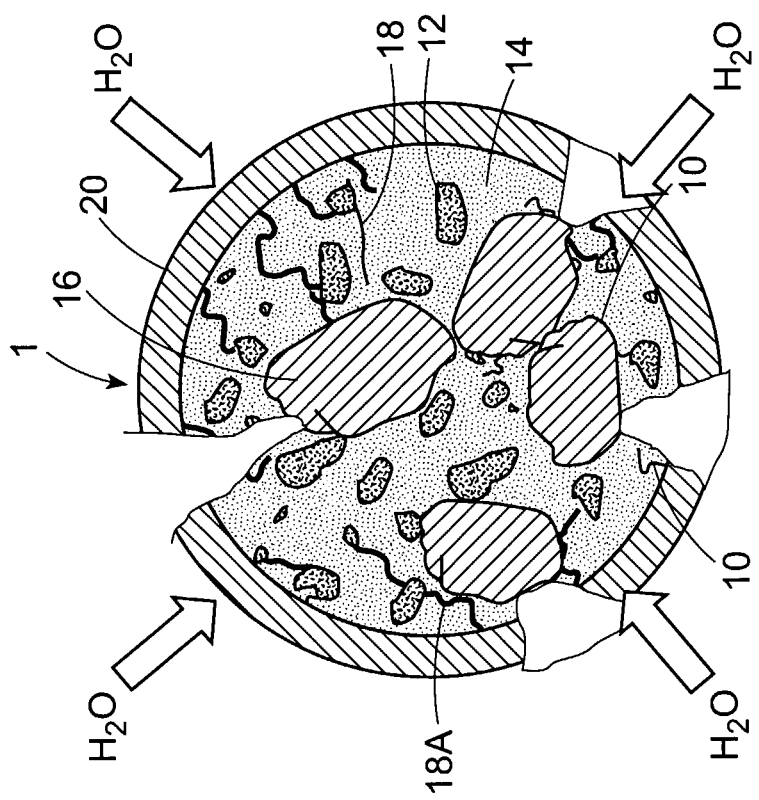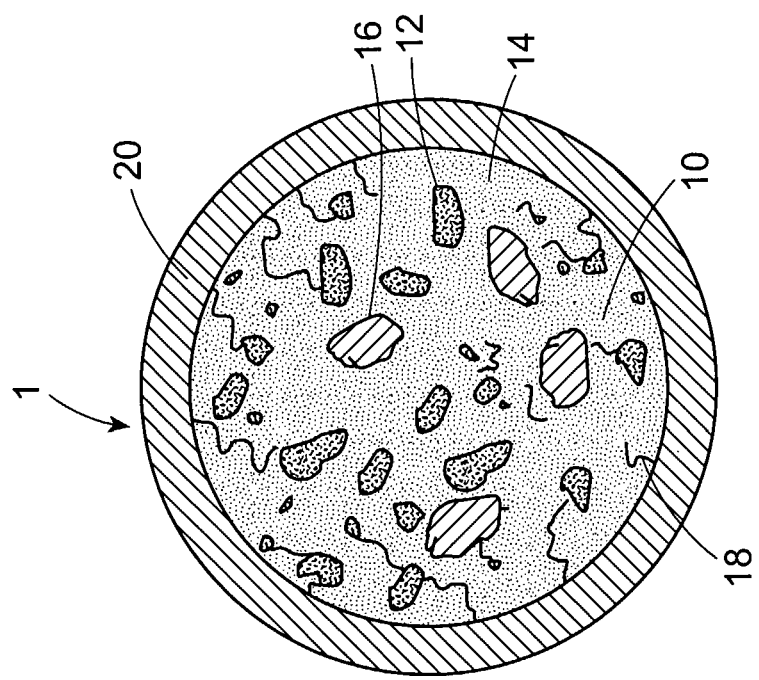

TASTE-MASKED DRUGS IN RUPTURING MULTIPARTICULATES

BACKGROUND OF THE INVENTION

Multiparticulates are well known pharmaceutical dosage forms that can be utilized for a wide range of applications. When taken orally, multiparticulates generally disperse freely in the gastrointestinal (GI) tract, maximize absorption, and minimize side effects. See, for example, Multiparticulate Oral Drug Delivery (Marcel Dekker, 1994), and Pharmaceutical Pelletization Technology (Marcel Dekker, 1989).

One application for multiparticulates is for delivery of drugs for which rapid delivery of the drug is desired for rapid onset of action. Such formulations must rapidly release the drug to the GI tract. For example, multiparticulates may be incorporated into fast-dissolving or disintegrating dosage forms (FDDFs) that rapidly release the drug when the dosage form is placed into the mouth.

In such formulations, when the drug has an unpleasant taste it is often desirable to delay the release of the drug until the multiparticulate has exited the mouth to improve patient compliance. In order to provide taste masking, the materials used to form the multiparticulates must be capable of satisfying two competing constraints. On the one hand, the materials need to be sufficiently robust so as to remain intact and provide taste masking in the mouth. On the other hand, the materials used to provide taste masking should be capable of quickly releasing the drug once the multiparticulate has exited the mouth. If the materials that provide taste masking are too robust, then the materials may undesirably inhibit or slow the release of the drug in the GI tract.

Another problem is that granules and multiparticulates can often present a gritty sensation in the patient's mouth. It is desired that the dosage form provide a pleasing feel in the mouth.

Another problem is that when such systems are used with drugs having a low aqueous solubility, the rate of release of drug from the multiparticulate is often low due to the low solubility of the drug.

There is therefore a need in the art to provide multiparticulate dosage forms that address one or more of the forgoing limitations.

BRIEF SUMMARY OF THE INVENTION

In a first aspect, the invention provides a pharmaceutical composition of multiparticulates, the multiparticulates comprising a core comprising a drug. The core is surrounded by a coating. The core comprises at least 30 wt % of a matrix material, and a water swellable swelling agent.

The composition satisfies the need to provide a robust taste-masking composition that is capable of quickly releasing the drug to the GI tract by providing a multiparticulate that combines a water-swellable swelling agent in the core with a coating. In one aspect, the coating is made from a water permeable, substantially drug-impermeable material that ruptures a short time after oral dosing. The coating provides taste masking of the drug when the multiparticulate enters the patient's mouth. However, once in the patient's mouth, water begins to diffuse through the coating into the core. The swelling agent imbibes water, causing the core to swell. The coating consequently expands until the stress exerted on the coating by the swollen core exceeds the tensile strength of the coating, at which time the coating ruptures so as to release the drug. By appropriate choice of coating and swelling agent, the time to rupture of the coating is long enough to avoid rupture in the patient's mouth, but short enough to provide quick release of the drug in the patient's stomach.

In another aspect, the coating is insoluble at the pH of the mouth, but soluble at the pH in the stomach. The coating provides taste masking of the drug when the multiparticulate enters the patient's mouth. However, once the multiparticulate enters the low pH of the gastric environment of the stomach, the coating dissolves, and the swelling agent imbibes water, causing the core to swell. Ultimately, the core disintegrates into a plurality of small pieces, from which the drug is rapidly released.

In a separate aspect, the invention provides a pharmaceutical composition of multiparticulates, the multiparticulates comprising a core comprising a drug. The core is surrounded by a coating. The core comprises a water-swellable swelling agent. The uncoated cores of the composition have a volume-weighted mean diameter of less than 150 µm.

This aspect of the invention has the advantage of utilizing small multiparticulates. Such small multiparticulates have been found to be more robust than larger multiparticulates. Any coating on such multiparticulates is less likely to become damaged when such multiparticulates are incorporated into compressed tablets or chewed. In addition, such small multiparticulates present a less gritty sensation in the mouth relative to larger multiparticulates or coated drug crystals.

In yet another aspect, the invention provides a process for making such multiparticulates comprising the steps:
(a) forming a molten mixture comprising a matrix material, a swelling agent, a drug and optionally a dissolution enhancer;
(b) atomizing the mixture of step (a) to form droplets;
(c) congealing the droplets of step (b) to form solid cores; and
(d) coating the cores of step (c) to form said multiparticulates.

Step (a) may be conducted by a variety of methods, including by melting, by extrusion, and by continuous milling. Steps (b) and (c) typically occur simultaneously, and may also be conducted by a variety of methods, including spray-congealing with the use of single-fluid, two-fluid, ultrasonic or mechanical vibrating nozzles; and by spinning-disk atomizers. Step (d) is conducted by conventional means, including various types of spray-coating.

The foregoing and other objectives, features, and advantages of the invention will be more readily understood upon consideration of the following detailed description of the invention.

BRIEF DESCRIPTION OF THE SEVERAL VIEWS OF THE DRAWINGS

FIG. 1 is a cross-sectional schematic of an exemplary multiparticulate of one embodiment of the invention placed in an aqueous environment.

FIG. 2 is a cross-sectional schematic of the same multiparticulate of FIG. 1 imbibing water from the aqueous environment and in the process of rupturing.

DETAILED DESCRIPTION OF PREFERRED EMBODIMENTS

Figure 3:
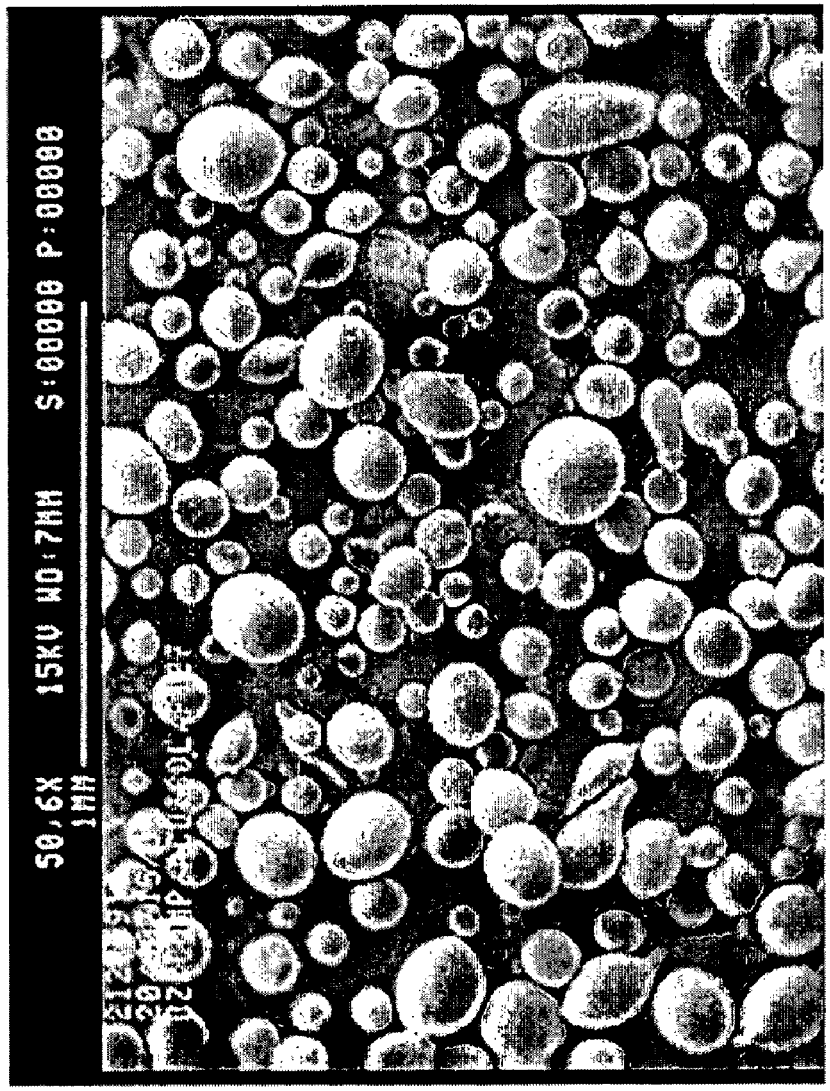
FIG. 3 is a photomicrograph of multiparticulates produced by the invention.

Referring to the drawings, there is shown in FIG. 1 a cross-sectional schematic of a multiparticulate 1 of one embodiment of the invention, comprising a core 10 surrounded by a coating 20. The core comprises at least one drug 12 substantially uniformly distributed in matrix material 14 that includes swelling agent 16. The multiparticulate delivers drug by imbibing water through the coating 20. The core may also include an optional dissolution enhancing agent 18 distributed as pores or channels throughout the matrix material 14. When placed in an aqueous fluid-containing environment such as a mouth or gastric environment, the multiparticulate permits aqueous fluid to pass through the coating 20 into the core 10, shown schematically in FIG. 2. The imbibed aqueous fluid 30 comes into contact with swelling agent 16, causing the same to swell and eventually cause rupture of the coating 20 to permit substantially complete release of drug 12. The coating and core constituents are chosen so that the rupture is sufficiently delayed in time that the coating ruptures in the stomach of a patient, rather than in the mouth. Multiparticulate rupture times vary from about 1 to about 10 minutes, with substantially all of the multiparticulates in a given dose ruptured within one hour. In this fashion, virtually all of the drug is released well after the multiparticulates have passed through the mouth.

In another embodiment (not shown), the coating is an anti-enteric coating. When placed into an aqueous fluid-containing environment with a pH greater than about 6, such as the mouth, the anti-enteric coating is insoluble, preventing release of drug into the mouth, thus providing taste-masking. When the multiparticulate is placed in an aqueous fluid-containing low-pH environment, such as gastric fluid, the anti-enteric coating is soluble and dissolves, exposing the core to the gastric environment and permitting aqueous fluid to enter into the core. The imbibed aqueous fluid comes into contact with the swelling agent, causing the same to swell and eventually causing disintegration of the core into a plurality of small pieces. The drug is then released from the disintegrated core pieces. The high surface area of the small pieces of core results in rapid release of the drug. In this fashion, virtually all of the drug is released well after the multiparticulates have passed through the mouth.

In yet another embodiment, the multiparticulate core comprises at least one low-solubility drug substantially uniformly distributed in a matrix material that includes a swelling agent. The multiparticulate core may also include an optional dissolution-enhancing agent distributed as pores or channels throughout the matrix material. When placed in an aqueous fluid-containing environment such as a mouth or gastric environment, aqueous fluid passes into the multiparticulate. The imbibed aqueous fluid comes into contact with the swelling agent, causing the same to swell and eventually cause disintegration of the multiparticulate core into a plurality of smaller pieces, resulting in a high surface area for release of the low-solubility drug.

Further details regarding the materials in the core, methods for making the core, and coatings to achieve a drug release rate that is sufficiently delayed to effectively taste-mask the drug and yet sufficiently fast to achieve substantially immediate release of the drug in the GI tract, are described in more detail below.

Drug Release Rate

In one embodiment, the multiparticulates of the invention are designed for a short delay in release, followed by substantially complete release of drug within one hour of introduction to a use environment. Such a release profile prevents release of the unpleasant-tasting drug in the mouth, yet provides substantially immediate release in the GI tract of an animal. As used herein, a "use environment" refers to either in vivo fluids, such as present in the buccal space or the GI tract of an animal, such as a mammal, and particularly a human; or to the in vitro environment of a test solution, such as a simulated mouth buffer (MB) or a simulated gastric buffer (GB). An appropriate simulated MB test solution is 0.05M $KH_2PO_4$ buffer adjusted to pH 7.3 with 10 M KOH. Appropriate GB test solutions include 0.01N HCl and 0.1N HCl. "Administration" to a use environment means, where the in vivo use environment is the mouth or GI tract, ingestion or other such means to deliver the multiparticulates. Where the use environment is in vitro, "administration" refers to placement or delivery of the composition or dosage form containing the multiparticulates to the in vitro test medium.

In one embodiment, the desired release rate from the coated multiparticulates in an environment of use is as follows. In general, the multiparticulates delay the release of the drug relative to a control composition consisting of the crystalline drug alone. The length of the delay of the release depends on the nature of the unpleasant tasting drug, since drugs that have very low taste thresholds will require longer delays. In general, the multiparticulates preferably release less than about 20 wt % of the drug, and more preferably less than about 10 wt % of the drug within the first minute after administration to a use environment, and preferably release less than about 25 wt %, and more preferably less than about 10 wt % within the first three minutes. However, the multiparticulates also provide substantially immediate release of the drug in the GI tract. Thus, the multiparticulates release at least about 70 wt %, preferably at least about 80 wt %, and more preferably at least about 90 wt % of the drug within one hour following administration to a use environment. Multiparticulates may be tested in a simulated MB test solution of 0.05M $KH_2PO_4$ buffer adjusted to pH 7.3 with 10M KOH to determine whether they meet the release criteria described above.

In another embodiment, the uncoated multiparticulate cores rapidly release a low solubility drug to an aqueous use environment. Thus, the uncoated multiparticulate cores release at least about 50 wt %, preferably at least about 60 wt %, more preferably at least about 70 wt %, and even more preferably at least about 80 wt %, and most preferably at least about 90 wt % of the low-solubility drug within one hour following administration to a use environment, where the use environment has a pH of less than about 5, such as a gastric use environment. Multiparticulate cores may be tested in a simulated gastric buffer (GB) test solution of 0.01 M HCl, pH 2.0, optionally containing 0.7 wt % NaCl, and optionally containing 0.5 wt % polysorbate 80 (sold as Tween™ 80, available commercially from ICI), at 37° C. The multiparticulate cores may also be evaluated in a MB to GB transfer test, wherein the multiparticulate cores are first administered to a MB test solution (described above) followed by administration to a GB test solution. In such tests, the multiparticulate cores release the low-solubility drug at the rates given above within one hour following administration to the GB test solution.

Multiparticulates

The multiparticulates of the present invention are small, having a mean diameter after coating of up to about 1 mm. A useful measure of their size that takes into account diameter and volume frequency is volume-weighted mean diameter. The volume-weighted mean assumes a gaussian size distribution, with approximately 85% of the particle volume being within about 30% of the reported size. The inventive multiparticulates after coating preferably have a volume-weighted mean diameter of less than 300 microns, and more preferably less than about 250 microns.

In a preferred embodiment, the multiparticulates are very small. The inventors have discovered that one problem associated with forming compressed chewable tablets using coated multiparticulates is that the coating may break during formation of the tablet. Such dosage forms often contain hard crystalline material, such as microcrystalline cellulose, saccharides such as sucrose or xylitol, or polyols like mannitol or sorbitol. It is believed that the compression of such hard crystalline materials into the multiparticulates causes the coating to break or fracture, defeating the taste masking provided by the coating. In addition, the coatings of large multiparticulates may break or fracture during chewing. However, the inventors have found that small multiparticulates are much less likely to experience broken coatings during compression or chewing. Preferably, such multiparticulates have a volume-weighted mean diameter after coating of less than 200 microns, and more preferably less than about 150 microns. The uncoated core of such multiparticulates have a volume-weighted mean diameter of less than 150 microns, more preferably less than about 125 microns, and even more preferably less than 100 microns. Such small multiparticulates also are more pleasing to patients, since such small multiparticulates present a smooth, rather than gritty sensation in the mouth, if such multiparticulates are even felt at all.

Drug

The core contains drug in an amount of up to about 65 wt % based upon the total mass of the uncoated core, preferably from 5 to 50 wt %, more preferably from 10 to 40 wt %, more preferably from 10 to 25 wt %, and most preferably from 15 to 25 wt %. The drug may be either crystalline or amorphous. The present invention finds particular utility for crystalline drugs, since the process used to form the multiparticulate is capable of maintaining the crystalline nature of the drug throughout the process. For crystalline drugs, the drug in the multiparticulate is preferably "substantially crystalline," meaning that at least 70 wt % of the drug is in the crystalline state. More preferably the drug is at least 80 wt % crystalline, and most preferably at least 90 wt %.

Examples of unpleasant-tasting drugs employed in the inventive multiparticulates include, without limitation, inorganic and organic compounds that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autocoid systems, alimentary and excretary systems, inhibitors of autocoids and histamine systems. Preferred classes of drugs include, but are not limited to, antacids, analgesics, anti-Alzheimer's disease agents, anti-anginals, anti-anxiety agents, anti-arrhythmics, anti-atherosclerotic agents, anti-bacterials, antibiotics, anti-clotting agents, anti-convulsants, anti-diarrheals, anti-depressants, anti-epileptics, anti-fungals, anti-histamines, anti-hypertensives, anti-impotence agents, anti-inflammatory agents, anti-neoplastics, anti-obesity agents, anti-psychotic agents, anti-tussives, anti-virals, autoimmune disorder agents, beta blockers, blood glucose-lowering agents, cardiac agents, cholesterol-reducing agents, cholesteryl ester transfer protein (CETP) inhibitors, triglyceride-reducing agents, cognitive enhancers, contraceptives, cough suppressants, cytotoxics, decongestants, diuretics, drugs for genito-urinary disorders, drugs for use in parkinsonism and related disorders, drugs for use in rheumatic disorders, hypnotics, glycogen phosphorylase inhibitors, minerals, vitamins, lipid-lowering drugs and sex hormones. Veterinary drugs may also be suitable for use with the present invention.

Each named drug should be understood to include the neutral form of the drug and pharmaceutically acceptable forms thereof. By "pharmaceutically acceptable forms" thereof is meant any pharmaceutically acceptable derivative or variation, including stereoisomers, stereoisomer mixtures, enantiomers, solvates, hydrates, isomorphs, polymorphs, pseudomorphs, salt forms and prodrugs. Specific examples of drugs include acetaminophen, albuterol, aminoguanidine, aminophylline, amitriptyline, amoxicillin, ampicillin, amlodipine, aspirin, azithromycin, barbiturates, berberine, benzhydrylpiperazines including cetirizine, caffeine, pantothenate, cephalosporins, chloramphenicol, chlordiazepoxide, chloroquine, chlorpheniramine, chlorpromazine, cimetidine, ciprofloxacin, clarithromycin, codeine, demerol, dextromethorphan, digitoxin, digoxin, diltiazem, diphenhydramine, diphenylhydantoin, doxazosin, doxylamine, eletriptan, enoxacin, epinephrine, erythromycin, ethylefrine, etinidine, famotidine, fluconazole, glipizide, guaifenesin, ibuprofen, indeloxazine, lidocaine, lomotil, loratadine, lupitidine, meclizine, methacholine, morphine, neostigmine, nifentidine, niperotidine, nizatidine, ofloxacin, paracetamol, pefloxacin, penicillin, phenobarbital, phenothiazine, phenylbutazone, phenylpropanolamine, pipemidic acid, pirbuterol hydrochloride, piroxicam, prednisolone, propranolol, pseudoephedrine, pyridonecarboxylic acid antibacterials, ranitidine, roxatidine, salicylic acid, sertraline, sildenafil, spironolactone, sulbactam sodium, sulfonamides, sulfotidine, sulpyrine, sultamicillin, tenidap, terfenadine, theophylline, trimethoprim, tuvatidine, valdelcoxib, zaltidine, and zonisamide. Preferred drugs for use with the present invention include: the benzhydrylpiperazines such as cetirizine; azithromycin; eletriptan; valdecoxib; and caffeine.

In one embodiment, the drug is a low-solubility drug. The term "low-solubility drug," means that the drug has a minimum aqueous solubility at physiologically relevant pHs (i.e., pH 1-8) of about 1 mg/mL or less. The drug may have an even lower aqueous solubility, such as less than about 0.5 mg/mL, less than about 0.1 mg/mL, and even less than about 0.05 mg/mL. In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (i.e., solutions with pH 1-8), including USP simulated gastric and intestinal buffers, and dose is in mg. Thus, a dose-to-aqueous solubility ratio may be calculated by dividing the dose (in mg) by the aqueous solubility (in mg/mL). Alternatively, the drug has a minimum aqueous solubility over the pH range of 6.5 to 7.5 of less than about 1 mg/mL, more preferably less than about 0.5 mg/mL, and even more preferably of less than about 0.1 mg/mL.

Specific examples of low-solubility drugs suitable for use in the present invention include amlodipine, azithromycin, celecoxib, digitoxin, digoxin, famotidine, fluconazole, glipizide, lidocaine, phenobarbital, prednisolone, sertraline, sildenafil citrate, spironolactone, and valdelcoxib.

Swelling Agent

The core also contains a water-swellable swelling agent that expands upon contact with aqueous fluids. The swelling agent is typically present as a separate phase from the matrix material and the drug. The swelling agent is preferably present from 1 to 40 wt %, based upon the mass of the uncoated core, more preferably from 5 to 35 wt %, more preferably from 5 to 30 wt %, more preferably from 10 to 30 wt %, and most preferably from 10 to 20 wt %.

The first requirement of the swelling agent is that it is highly swelling. In one embodiment, as the multiparticulate imbibes water through the coating, the swelling agent must expand a sufficient amount to rupture the coating. The swelling agent should cause a sufficient expansion in volume of the multiparticulate that the coating is stretched beyond the yield point of the coating and fractures. In another embodiment, the swelling agent expands sufficiently to disintegrate the core into a plurality of small pieces. Preferably, the swelling agent expands in volume by a factor of at least about 2, more preferably at least about 3.5, and even more preferably at least about 5 in the gastric use environment. The following test may be used to determine the swelling ratio of water-swellable materials. The swelling material is compressed into a compact using a 13/32-inch die, the tablet having a strength ranging from 3 to 16 Kp/cm$^2$. This compressed material is then placed into a glass cylinder of approximately the same inside diameter as the tablet and the volume of the tablet is determined. Next, the glass cylinder is filled with simulated gastric buffer consisting of 0.01 M HCl and 0.12 M NaCl in deionized water. The glass cylinder and test media are all equilibrated at a constant temperature of 37° C. The volume of the tablet is determined at several time intervals. The ratio of the volume of the tablet after reaching a constant height to that of the volume of the dry tablet is the swelling ratio, or swelling factor, of the material.

In addition, the swelling agent should swell rapidly. In one embodiment, rapid swelling is desired for two reasons. First, the multiparticulate should release the drug quickly to the patient's stomach. Therefore, swelling should be fast enough so that the coating ruptures within the release rates described above. Second, rapid swelling is necessary to rupture the coating. If the swelling agent swells too slowly, the coating may also slowly swell and expand rather than rupture. In another embodiment, rapid swelling is desired to ensure the core rapidly disintegrates into a plurality of small pieces, allowing release of the drug at the rates described above. Using the test described above, the rate at which swelling occurs may be determined. Preferably, the swelling material expands in volume by a factor of at least about 2 in the gastric use environment within one hour, more preferably within about 30 minutes, and most preferably within about 15 minutes.

Finally, the swelling agent should also be such that it may be blended with the molten matrix material (described below) to form a flowable suspension. The swelling agent should be present as a separate phase in the core, so that when the core imbibes water, the swelling agent swells and ruptures the coating or disintegrates the core. Preferably, the swelling agent does not dissolve in the core. Thus, when the multiparticulates are formed using a melt method, the swelling material remains as a solid suspended in the molten matrix. If the swelling agent does dissolve, it should phase separate into large domains of relatively pure swelling agent when the core congeals.

Exemplary swelling agents that are both highly swelling and swell rapidly include polymers such as sodium starch glycolate (commercially available as EXPLOTAB from Edward Mendell Co.), croscarmellose sodium (commercially available as AC-DI-SOL from FMC Corporation of Philadelphia, Pa.), and crospovidone. These polymers also are capable of remaining as a separate solid phase in a molten matrix.

Matrix Materials

The core also comprises a matrix material. The matrix material serves two functions. First, the matrix material binds the water-swellable swelling agent and crystalline drug together. Second, the matrix allows the uncoated core to be formed into a relatively smooth, round sphere that is amenable to coating. The matrix material has the following physical properties: the matrix preferably melts at a lower temperature than the drug; does not substantially dissolve the drug; has a sufficiently low viscosity in the molten state to form microspheres, as detailed below; and rapidly congeals to a solid when cooled below its melting point.

The multiparticulate cores made by the process of the invention are solid at 25° C. but are essentially drug particles, swelling agent particles, and optionally other excipients, encapsulated within a continuous phase of matrix material. Because of this, a sufficient amount of matrix material must be present so as to encapsulate the drug and swelling agent to form smooth and spherical multiparticulates, which are more easily coated by conventional coating processes than irregularly-shaped ones. The matrix is preferably present in the core from about 30 to 95 wt % based on the mass of the uncoated core, more preferably from 50 to 60 wt %.

The matrix material or mixture of materials is solid at 25° C. but should have a melting point below that of the melting point of the drug. Although the term "melt" generally refers to the transition of a crystalline material from its crystalline to its liquid state, which occurs at its melting point, and the term "molten" generally refers to such a crystalline material in its fluid state, as used herein, the terms are used more broadly. In the case of "melt," the term is used to refer to the heating of any material or mixture of materials sufficiently that it becomes fluid in the sense that it may be pumped or atomized in a manner similar to a crystalline material in the fluid state. Likewise "molten" refers to any material or mixture of materials that is in such a fluid state. By selecting a matrix material that has a melt temperature below that of the drug, a molten mixture may be formed at a temperature below that of the melting point of the drug. This allows the drug to remain substantially crystalline while being formed into microspheres. Preferably, the matrix material becomes molten at a temperature that is 10° C. less than the melting point of the drug, more preferably at least 20° C. less than the melting point of the drug, and even more preferably at least 30° C. less than the melting point of the drug.

In addition, drug should have a low solubility in the molten matrix material. Dissolution of the drug can reduce the crystallinity of the drug in the finished microsphere and compromise its chemical and physical stability. The drug should have a solubility in the molten matrix material of less than about 30 wt %, more preferably less than about 20 wt %, and even more preferably less than about 10 wt %.

The matrix material or mixture of materials must also be able to rapidly form a solid material when cooled below its melting point. When the molten mixture is atomized as discussed below, a droplet of the molten mixture should cool and solidify while it is in flight between the atomizer and the collection device. This time period may be from approximately 0.1 to 60 seconds. Therefore, the matrix material should be chosen so that the rate of cooling and solidification of the droplet is sufficiently large for solidification to occur within this time period. For amorphous matrix materials, the matrix material should have a glass transition temperature that is greater than the temperature to which the molten matrix material is being cooled during atomization. Since the molten material may be cooled and stored at room temperature, the matrix material preferably has a glass transition temperature that is at least 40° C., more preferably at least 50° C., and even more preferably at least 60° C. This causes the molten matrix material to change from flowable to hard and glassy as it is cooled during atomization. For matrix materials that may crystallize, a desired property is for the matrix material to rapidly crystallize to a solid when cooled during atomization below its melting point.

Exemplary matrix materials include highly purified forms of waxes, such as Carnauba wax, white and yellow beeswax, microcrystalline wax, and paraffin wax; long-chain alcohols, such as stearyl alcohol, cetyl alcohol and polyethylene glycol; poloxamers; polyoxyethylene alkyl ethers; long-chain fatty acid esters (also known as fats), such as glyceryl monooleate, glyceryl monostearate, glyceryl palmitostearate, polyethoxylated castor oil derivatives, mixtures of mono-, di-, and tri-alkyl glycerides, including mixtures of glyceryl mono-, di-, and tribehenate, glyceryl tristearate, glyceryl tripalmitate and hydrogenated vegetable oils, including hydrogenated cottonseed oil; glycolized fatty acid esters, such as polyethylene glycol stearate and polyethylene glycol distearate; short to medium chain fatty acid esters, such as isopropyl palmitate, isopropyl myristate, triethyl citrate, lecithin, triacetin, and dibutyl sebacate; polysorbates; carboxylic acids such as stearic acid, benzoic acid, citric acid, fumaric acid, lactic acid, and maleic acid; and mixtures thereof. Especially preferred matrix materials are an alkyl-containing glycerol such as a mixture of mono-, di- and triglyceryl behenates (commercially available as COMPRITOL 888 from Gattefosé Corporation of Westwood, N.J.); and hydrogenated cottonseed oil (commercially available as LUBRITAB from Edward Mendell Co. of Patterson, N.Y.). The matrix material may comprise mixtures of materials, such as mixtures of any of the foregoing.

Excipients

The core may also contain a variety of excipients, present in the core in an amount of from 0 to 40 wt %, based upon the mass of the uncoated core.

One preferred excipient is a dissolution enhancer, which may be used to increase the rate of water uptake by the core and consequent expansion of the swelling agent. The dissolution enhancer may be in a separate phase or a single phase with the matrix material. Preferably, at least a portion of the dissolution enhancer is phase-separated from the matrix material. As shown in FIG. 1, the dissolution-enhancer 18 is present as a separate phase in the matrix material 14, forming pores or channels throughout the matrix material. As shown in FIG. 2, as water enters the core 12, the dissolution-enhancer dissolves, expanding the channels and causing the water to more rapidly enter the core to cause the swelling agent 16 to expand.

In general, dissolution enhancers are amphiphilic compounds and are generally more hydrophilic than the matrix materials. Examples of dissolution-enhancing agents include alcohols, such as stearyl alcohol, cetyl alcohol, and polyethylene glycol; poloxamers; docusate salts; polyoxyethylene alkyl ethers; polyoxyethylene alkyl esters; polyoxyethylene castor oil derivatives; polysorbates; sodium lauryl sulfate; sorbitan monoesters; mixtures of mono-, di- and tri-alkyl glycerides and mono- and di-fatty acid esters of polyethylene glycol; sugars, such as glucose, xylitol, sorbitol and maltitol; salts, such as sodium chloride, potassium chloride, lithium chloride, calcium chloride, magnesium chloride, sodium sulfate, potassium sulfate, sodium carbonate, magnesium sulfate and potassium phosphate; and amino acids, such as alanine and glycine; and mixtures thereof. A preferred surfactant-type dissolution-enhancer is a poloxamer (commercially available as the LUTROL or PLURONIC series from BASF Corp.).

The core may also contain other optional excipients, such as agents that inhibit or delay the release of drug from the multiparticulates. Such dissolution-inhibiting agents are generally hydrophobic and include dialkylphthalates such as dibutyl phthalate, and hydrocarbon waxes, such as microcrystalline wax and paraffin wax.

Another useful class of excipients comprises materials that may be used to adjust the viscosity of the molten feed used to form the multiparticulates. Such viscosity-adjusting excipients will generally make up 0 to 25 wt % of the multiparticulate, based on the total mass of the uncoated multiparticulate. The viscosity of the molten feed is a key variable in obtaining multiparticulates with a narrow particle size distribution. For example, when a spinning-disk atomizer is employed, it is preferred that the viscosity of the molten mixture be at least about 1 cp and less than about 10,000 cp, more preferably at least 50 cp and less than about 1000 cp. If the molten mixture has a viscosity outside these preferred ranges, a viscosity-adjusting agent can be added to obtain a molten mixture within the preferred viscosity range. Examples of viscosity-reducing excipients include stearyl alcohol, cetyl alcohol, low molecular weight polyethylene glycol (i.e., less than about 1000 daltons), isopropyl alcohol, and water. Examples of viscosity-increasing excipients include microcrystalline wax, paraffin wax, synthetic wax, high molecular weight polyethylene glycols (i.e., greater than about 5000 daltons), ethyl cellulose, hydroxypropyl cellulose, hydroxypropyl methyl cellulose, methyl cellulose, silicon dioxide, microcrystalline cellulose, magnesium silicate, sugars, and salts.

Other excipients may be added to adjust the release characteristics of the multiparticulates or to improve processing and will typically make up 0 to 50 wt % of the multiparticulate, based on the total mass of the multiparticulate. For example, an acid or base may be included in the composition to modify the rate at which drug is released in an aqueous use environment. Examples of acids or bases that can be included in the composition include citric acid, adipic acid, malic acid, succinic acid, tartaric acid, di- and tribasic sodium phosphate, di- and tribasic calcium phosphate, mono-, di-, and triethanolamine, sodium bicarbonate and sodium citrate dihydrate. Still other excipients may be added to reduce the static charge on the multiparticulates. Examples of such anti-static agents include talc and silicon dioxide. Flavorants, colorants, and other excipients may also be added in their usual amounts for their usual purposes.

In a preferred embodiment, the uncoated core components are preferably present in the following amounts, based upon the total mass of the core:
- (i) drug up to 65 wt %, more preferably from 5 to 50 wt %, still more preferably from 10 to 40 wt %, more preferably from 10 to 25 wt %, and most preferably from 15 to 25 wt %;
- (ii) swelling agent from 1 to 40 wt %, more preferably from 5 to 35 wt %, more preferably from 5 to 30 wt %, more preferably from 10 to 30 wt %, and most preferably from 10 to 20 wt %;
- (iii) matrix material from 30 to 95 wt %, more preferably 30 to 85 wt %, more preferably 40 to 70 wt %; and
- (iv) optional dissolution enhancer from 0 to 20 wt %, more preferably 2 to 15 wt %.

Forming the Cores

The process used to form the cores comprises the steps of (a) forming a molten mixture comprising drug and the other core components, (b) atomizing the molten mixture of step (a) to form droplets, and (c) congealing the droplets from step (b) to form cores.

The matrix material, drug, swelling agent and other optional core components are combined to form a molten mixture in which the drug and swelling agent are suspended. As previously noted, "molten mixture" refers to a mixture that is treated by heat, pressure or shear forces to the point that the mixture becomes sufficiently fluid that the mixture may be formed into droplets or atomized. Generally the mixture is molten in the sense that it will flow when subjected to one or more forces such as pressure, shear, and centrifugal force, such as that exerted by a centrifugal or spinning-disk atomizer. Thus, the mixture may be considered "molten" when the mixture, as a whole, is sufficiently fluid that it may be atomized.

The temperature of the molten mixture is maintained below that of the melting point of the drug but sufficiently high to form the molten mixture. In addition, the temperature of the molten matrix should be sufficiently low so that the solubility of the drug in the matrix material is less than 30 wt %.

Virtually any process may be used to form the molten mixture. One method involves heating the matrix material in a tank until it is fluid and then adding the drug and swelling agent. Generally, the matrix material is heated to a temperature of about 10° C. or more above the temperature at which it becomes fluid. Alternatively, both the drug and the matrix material may be added to the tank and the mixture heated until the molten mixture has become fluid.

An alternative method of preparing the molten mixture is to use two tanks, melting a first matrix material in one tank and a second in another. The drug is added to one of these tanks and mixed as described above. The two melts are then pumped through an in-line static mixer or extruder to produce a single molten mixture that is directed to the atomization process described below.

Once the molten mixture has become fluid and the drug has been added, the mixture is mixed to ensure the drug is substantially uniformly distributed therein. Mixing is generally done using mechanical means, such as overhead mixers, magnetically driven mixers and stir bars, planetary mixers, and homogenizers. Optionally, the contents of the tank can be pumped out of the tank and through an in-line, static mixer or extruder and then returned to the tank. The amount of shear used to mix the molten mixture should be sufficiently high to ensure substantially uniform distribution of the drug in the molten mixture. However, it is preferred that the shear not be so high such that the form of the drug is changed, i.e., so as to cause a portion of the crystalline drug to become amorphous or change to a new crystalline form of drug. Generally, it is preferred to limit the mixing time to near the minimum necessary to suspend the crystalline drug substantially uniformly throughout the molten mixture.

Another method that can be used to prepare the molten mixture is to use a continuously stirred tank system. In this system, the drug and matrix material are continuously added to a heated tank equipped with means for continuous stirring, while the molten mixture is continuously removed from the tank. The drug is typically added in solid form and may be pre-heated prior to addition to the tank. The matrix material may also be preheated or even pre-melted prior to addition to the continuously stirred tank system. A wide variety of mixing methods can be used with such a system, such as those described above.

The molten mixture may also be formed using a continuous mill, such as a Dyno® Mill wherein solid drug and carrier are fed to the mill's grinding chamber containing grinding media, such as beads with diameters of 0.25 to 5 mm. The grinding chamber typically is jacketed so heating or cooling fluid may be circulated around the chamber to control the temperature in the chamber. The molten mixture is formed in the grinding chamber, and exits the chamber through a separator to remove the grinding media from the molten mixture.

An especially preferred method of forming the molten mixture is by an extruder. By "extruder" is meant a device or collection of devices that creates a molten extrudate by heat and/or shear forces and/or produces a uniformly mixed extrudate from a solid and/or liquid (e.g., molten) feed. Such devices include, but are not limited to single-screw extruders; twin-screw extruders, including co-rotating, counter-rotating, intermeshing, and non-intermeshing extruders; multiple screw extruders; ram extruders, consisting of a heated cylinder and a piston for extruding the molten feed; gear-pump extruders, consisting of a heated gear pump, generally counter-rotating, that simultaneously heats and pumps the molten feed; and conveyor extruders. Conveyer extruders comprise a conveyer means for transporting solid and/or powdered feeds, such as a screw conveyer or pneumatic conveyer, and a pump. At least a portion of the conveyer means is heated to a sufficiently high temperature to produce the molten mixture. The molten mixture may optionally be directed to an accumulation tank, before being directed to a pump, which directs the molten mixture to an atomizer. Optionally, an in-line mixer may be used before or after the pump to ensure the molten mixture is substantially homogeneous. In each of these extruders the molten mixture is mixed to form a uniformly mixed extrudate. Such mixing may be accomplished by various mechanical and processing means, including mixing elements, kneading elements, and shear mixing by backflow. Thus, in such devices, the composition is fed to the extruder, which produces a molten mixture that can be directed to the atomizer.

In one embodiment, the composition is fed to the extruder in the form of a solid powder. The powdered feed can be prepared using methods well known in the art for obtaining powdered mixtures with high content uniformity. See *Remington's Pharmaceutical Sciences* (16th ed. 1980). Generally, it is desirable that the particle sizes of the drug and carrier be similar to obtain a uniform blend. However, this is not essential to the successful practice of the invention.

Once the molten mixture has been formed, it is delivered to an atomizer that breaks the molten mixture, or feed, into small droplets. Virtually any method can be used to deliver the molten mixture to the atomizer, including the use of pumps and various types of pneumatic devices such as pressurized vessels or piston pots. When an extruder is used to form the molten mixture, the extruder itself can be used to deliver the molten mixture to the atomizer. Typically, the molten mixture is maintained at an elevated temperature while delivering the mixture to the atomizer to prevent solidification of the mixture and to keep the molten mixture flowing.

Atomization may be conducted in a number of ways, including (1) by "pressure" or single-fluid nozzles; (2) by two-fluid nozzles; (3) by ultrasonic nozzles; (4) by mechanical vibrating nozzles; or (5) by centrifugal or spinning-disk atomizers. Detailed descriptions of atomization processes can be found in Lefebvre, *Atomization and Sprays* (1989) and in *Perry's Chemical Engineers' Handbook* (7th Ed. 1997), the disclosures of which are incorporated herein by reference.

There are many types and designs of pressure nozzles, which generally deliver the molten mixture at high pressure to an orifice. The molten mixture exits the orifice as a filament or as a thin sheet that breaks up into filaments, which subsequently break up into droplets. The operating pressure drop across the pressure nozzle ranges from 1 barg to 70 barg, depending on the viscosity of the molten feed, the size of the orifice, and the desired size of the multiparticulates.

In two-fluid nozzles, the molten mixture is contacted with a stream of gas, typically air or nitrogen, flowing at a velocity sufficient to atomize the molten mixture. In internal-mixing configurations, the molten mixture and gas mix inside the nozzle before discharging through the nozzle orifice. In external-mixing configurations, high velocity gas outside the nozzle contacts the molten mixture. The pressure drop of gas across such two-fluid nozzles typically ranges from 0.5 barg to 10 barg.

In ultrasonic nozzles, the molten mixture is fed through or over a transducer and horn, which vibrates at ultrasonic frequencies, atomizing the molten mixture into small droplets. In mechanical vibrating nozzles, the molten mixture is fed through a needle vibrating at a controlled frequency, atomizing the molten mixture into small droplets. In both cases, the particle size produced is determined by the liquid flow rate, frequency of ultrasound or vibration, and the orifice diameter.

A preferred method of atomizing is by centrifugal atomizers, also known as rotary atomizers or spinning-disk atomizers, whereby the molten mixture is fed onto a rotating surface, where it is caused to spread out by centrifugal force. The rotating surface may take several forms, examples of which include a flat disk, a cup, a vaned disk, and a slotted wheel. The surface of the disk may also be heated to aid in formation of the multiparticulates. Several mechanisms of atomization are observed with flat-disk and cup centrifugal atomizers, depending on the flow of molten mixture to the disk, the rotation speed of the disk, the diameter of the disk, the viscosity of the feed, and the surface tension and density of the feed. At low flow rates, the molten mixture spreads out across the surface of the disk and when it reaches the edge of the disk, forms a discrete droplet, which is then flung from the disk. As the flow of molten mixture to the disk increases, the mixture tends to leave the disk as a filament, rather than as a discrete droplet. The filament subsequently breaks up into droplets of fairly uniform size. At even higher flow rates, the molten mixture leaves the disk edge as a thin continuous sheet, which subsequently disintegrates into irregularly sized filaments and droplets. The diameter of the rotating surface generally ranges from 2 cm to 50 cm, and the rotation speeds range from 500 rpm to 100,000 rpm or higher, depending on the desired size of the multiparticulates.

Once the molten mixture has been atomized, the droplets are congealed, typically by contact with a gas or liquid at a temperature below the solidification temperature of the droplets. Typically, it is desirable that the droplets are congealed in less than about 60 seconds, preferably in less than about 10 seconds, more preferably in less than about 1 second. The congealing step often occurs in an enclosed space to simplify collection of the multiparticulates. In such cases, the temperature of the congealing media (either gas or liquid) will increase over time as the droplets are introduced into the enclosed space. Thus, a cooling gas or liquid is often circulated through the enclosed space to maintain a constant congealing temperature.

The cores of the multiparticulates are preferably made by a melt-congeal process comprising the steps of melting the matrix material and dispersing therein the drug, swelling agent and optional dissolution enhancer; and directing the so-formed melt to an atomizing apparatus, preferably a spinning disk atomizer operating at 1500 to 8000 rpm, preferably 2500 to 6500 rpm, whereby small droplets of the melt are formed and radially dispersed by centrifugal force into a cooling chamber where they rapidly lose heat and congeal into small, generally spherical particles.

Coating

In one embodiment, the coating 20 comprises a water-permeable, substantially drug-impermeable polymer capable of permitting imbibition of aqueous-based fluid in a mouth or gastric environment. The coating has a low drug permeability to minimize drug release into the mouth or buccal use environment when the coating is intact. The coating is typically present in an amount of from 10 to 60 wt % of the mass of the uncoated cores, preferably 15 to 50 wt %, and more preferably 20 to 40 wt %. An important property of the coating is that it has sufficiently low ductility and tensile strength that it ruptures when the core swells rather than merely expanding with the core. An additional property of the coating when used with compressed dosage forms such as chewable tablets is that it is sufficiently strong and ductile to resist damage during compaction.

In order to provide taste masking, coating materials should either be substantially water-insoluble, meaning a solubility in water at ambient temperature of less than 0.1 mg/ml, or should have sufficiently slow dissolution in water so that the coating ruptures prior to dissolution of a significant portion of the coating. Preferred water-insoluble coatings include cellulose ethers such as ethyl cellulose, polymethacrylates, polyalkenes, polyethers, polysulfones, polyether sulfones, polystyrenes, polyvinyl ethers, polyvinyl halides, paraffin wax, microcrystalline wax, and synthetic wax. A particularly preferred cellulose ether is ethyl cellulose (commercially available as SURELEASE from Colorcon of West Point, Pa.). A particularly preferred polymethycrylate is a 2:1 copolymer of ethyl acrylate and methyl methacrylate (commercially available as EUDRAGIT NE from Rohm Pharma of Darmstadt, Germany). An exemplary coating solution using Eugragit NE30D contains 12.5% poly (ethyl acrylate, methyl methacrylate), 10% talc, and 77.5% water. The composition of the final dry coating (water removed) is 55% poly (ethyl acrylate, methyl methacrylate), and 45% talc.

In another embodiment, the coating is an anti-enteric coating. By "anti-enteric" coating is meant a coating comprising a pharmaceutically acceptable polymer having a solubility of less than 10 mg/mL in aqueous solutions having a pH of greater than about 6, and a solubility of more than 10 mg/mL in aqueous solutions having a pH of less than about 5. Suitable anti-enteric polymers include, for example, aminoalkyl methacrylate copolymers such as a butyl methacrylate/(2-dimethylaminoethyl)methacrylate/methyl methacrylate copolymer (such as Eudragit®) E manufactured by Rohm Pharma of Darmstadt, Germany) and polyvinylacetal diethylaminoacetate (such as AEA™ manufactured by Sankyo, Tokyo, Japan). An exemplary coating solution using Eudragit®) E contains 8 wt % EUDRAGIT® E PO, 55 wt % isopropyl alcohol, and 37 wt % acetone.

The coating solution may also comprise pore-formers, non-solvents, or plasticizers in any amount so long as the polymer remains substantially soluble at the conditions used to form the coating solution and so long as the finished coating remains water-permeable and ruptures as a result of expansion of the core. Pore-formers and their use in fabricating coatings are described in U.S. Pat. Nos. 5,612,059 and 5,698,220, the pertinent disclosures of which are incorporated herein. The term "pore former," as used herein, refers to a material added to the coating solution that has low or no volatility relative to the solvent such that it remains as part of the coating following the coating process but that is sufficiently water swellable or water soluble such that, in the aqueous use environment it provides a water-filled or water-swollen channel or "pore" to allow the passage of water thereby enhancing the water permeability of the coating. Suitable pore-formers include polyethylene glycol (PEG), PVP, PEO, HEC, HPMC and other aqueous-soluble cellulosics, water-soluble acrylate or methacrylate esters, polyacrylic acid and various copolymers and mixtures of these water soluble or water swellable polymers. Enteric polymers such as cellulose acetate phthalate (CAP) and HPMCAS are included in this class of polymers.

The coating solution may also include a non-solvent to increase the porosity of the coating. By "non-solvent" is meant any material added to the coating solution that substantially dissolves in the coating solution and reduces the solubility of the coating polymer or polymers in the solvent. Porous coatings have higher water permeability than an equivalent weight of a coating of the same composition that is not porous and this porosity, when the pores are gas filled, as is typical when the non-solvent is volatile, is indicated by a reduction in the density of the coating (mass/volume). Although not wishing to be bound by any particular mechanism of pore formation, it is generally believed that addition of a non-solvent imparts porosity to the coating during evaporation of solvent by causing the coating solution to undergo liquid-liquid phase separation prior to solidification. Suitable non-solvents are any materials that have appreciable solubility in the solvent and that lower the coating polymer solubility in the solvent. The preferred non-solvent depends on the solvent and the coating polymer chosen. In the case of using a volatile polar coating solvent such as acetone or methyl ethyl ketone, suitable non-solvents include water, glycerol, ethylene glycol and its low molecular-weight oligomers (e.g., less than about 1,000 daltons), propylene glycol and its low molecular weight oligomers (e.g., less than about 1,000 daltons), $C_1$ to $C_4$ alcohols such as methanol or ethanol, ethylacetate, acetonitrile and the like.

The coating may include conventional plasticizers, including dibutyl phthalate; dibutyl sebacate; diethyl phthalate; dimethyl phthalate; triethyl citrate; benzyl benzoate; butyl and glycol esters of fatty acids; mineral oil; oleic acid; stearic acid; cetyl alcohol; stearyl alcohol; castor oil; corn oil; coconut oil; and camphor oil; and other excipients such as antitack agents, glidants, etc. For plasticizers, triethyl citrate, coconut oil and dibutyl sebacate are particularly preferred.

The coating can be formed using solvent-based and hot-melt coating processes. In solvent-based processes, the coating is made by first forming a solution or suspension comprising the solvent, the coating material and optional coating additives. The coating materials may be completely dissolved in the coating solvent, or only dispersed in the solvent as an emulsion or suspension or a combination of the two. Latex dispersions are an example of an emulsion or suspension that may be useful as in a solvent-based coating process. In one aspect, the solvent is a liquid at room temperature. Preferably, the solvent is a volatile solvent, meaning that the solvent has a boiling point of less than about 150° C. at ambient pressure, although small amounts of solvents with higher boiling points can be mixed with volatile solvents and acceptable results still obtained. Examples of solvents suitable for use in applying a coating include alcohols, such as methanol, ethanol, isomers of propanol and isomers of butanol; ketones, such as acetone, methylethyl ketone and methyl isobutyl ketone; hydrocarbons, such as pentane, hexane, heptane, cyclohexane, methylcyclohexane, and octane; ethers, such as methyl tert-butyl ether, ethyl ether and ethylene glycol monoethyl ether; chlorocarbons, such as chloroform, methylene dichloride and ethylene dichloride; tetrahydrofuran; dimethylsulfoxide; N-methyl pyrrolidinone; acetonitrile; water; and mixtures thereof.

Coating may be conducted by conventional techniques, such as by pan coaters, rotary granulators and fluidized bed coaters such as top-spray, tangential-spray or bottom-spray (Würster coating), most preferably the latter.

In a preferred solvent-based process for forming the coating, a Würster fluidized bed system is used. In this system, a cylindrical partition (the Würster column) is placed inside a conical product container in the apparatus. Air passes through a distribution plate located at the bottom of the product container to fluidize the multiparticulates, with the majority of the upward moving air passing through the Würster column. The multiparticulates are drawn into the Würster column, which is equipped with an atomizing nozzle that sprays the coating solution upward. The multiparticulates are coated as they pass through the Würster column, with the coating solvent being removed as the multiparticulates exit the column. Since the multiparticulate cores of the invention are typically smaller than multiparticulates made by other methods, they are more susceptible to agglomeration and to build-up of static charges. To reduce such static charges in order to successfully apply a uniform coating, humidification of the fluidizing gas is helpful. Other process variables such as fluidizing gas flow rate, design of air distribution plate, and Würster column height can all be adjusted to optimize the quality of the fluidization and minimize agglomeration. Dry-blending a glidant such as talc onto the multiparticulates immediately after coating or while they are still in the coating apparatus is another method of preventing agglomeration during coating.

A top-spray method can also be used to apply the coating. In this method, coating solution is sprayed down onto the fluidized cores. The solvent evaporates from the coated cores and the coated cores are re-fluidized in the apparatus. Coating continues until the desired coating thickness is achieved.

The coating may also be applied using a hot-melt coating technique. In this method, the coating excipients and additives are first melted and then sprayed onto the cores. Typically, the hot-melt coating is applied in a fluidized bed equipped with a top-spray arrangement.

Another method for applying a hot-melt coating to the cores is to use a modified melt-congeal method. In this method, the cores are suspended in the molten coating excipients, the melting point of the cores being greater than the melting point of the coating excipients. This suspension is then formed into droplets comprising the cores surrounded by the coating excipients. The droplets are typically formed by an atomizer, such as a rotary or spinning-disk atomizer. The droplets are then cooled to congeal the coating, forming the coated multiparticulates.

Dosage Forms

The multiparticulates may be administered using any known dosage form that is taken orally, including: powders or granules; tablets; chewable tablets; capsules; unit dose packets, sometimes referred to in the art as "sachets" or "oral powders for constitution" (OPC); syrups; and suspensions. When the dosage form is an OPC, syrup, suspension or the like, in which the multiparticulate is suspended in a liquid when administered to the patient, the dosage form is administered to the patient sufficiently quickly so that the multiparticulates do not rupture or disintegrate in the dosage form or the patient's mouth.

Conventional formulation excipients may be employed in the compositions of this invention, including those excipients well-known in the art. Generally, excipients such as fillers, disintegrating agents, pigments, binders, lubricants, glidants, flavorants, and so forth may be used for customary purposes and in typical amounts without adversely affecting the properties of the compositions. These excipients may be utilized after the multiparticulate compositions have been formed, in order to formulate the compositions into tablets, capsules, suspensions, powders for suspension, and the like.

Examples of additional tastemasking agents include sweeteners such as aspartame, compressible sugar, dextrates, lactose, mannitol, maltose, sodium saccharin, sorbitol, and xylitol, and flavors such as banana, cherry, eucalyptus oil, menthol, orange, peppermint oil, raspberry, strawberry, watermelon, and wild cherry.

Examples of dosage form excipients, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose.

Examples of surface active agents include sodium lauryl sulfate and polysorbate 80.

Examples of disintegrants include sodium starch glycolate, sodium carboxymethyl cellulose, calcium carboxymethyl cellulose, croscarmellose sodium, crospovidone (polyvinylpolypyrrolidone), methyl cellulose, microcrystalline cellulose, powdered cellulose, starch, pregelatinized starch, and sodium alginate.

Examples of tablet binders include acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropyl methyl cellulose, methyl cellulose, liquid glucose, maltodextrin, polymethacrylates, povidone, pregelatinized starch, sodium alginate, starch, sucrose, tragacanth, and zein.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of glidants include silicon dioxide, talc and cornstarch.

Chewable tablets for oral administration are a preferred dosage form. Such a dosage form may be formed by combining the multiparticulates with compressible sugar, a filler such as microcrystalline cellulose, a disintegrant, and flavorants. These ingredients may be mixed together followed by addition of a lubricant such as magnesium stearate, followed by further mixing. The tablet mixture may be compressed, resulting in tablets with a hardness of 1-9 kP.

Without further elaboration, it is believed that one of ordinary skill in the art can, using the foregoing description, utilize the present invention to its fullest extent. Therefore, the following specific embodiments are to be construed as merely illustrative and not restrictive of the scope of the invention. Those of ordinary skill in the art will understand that variations of the conditions and processes of the following examples can be used.

EXAMPLE 1

Multiparticulate cores were formed comprising 20 wt % of the bitter-tasting antihistamine cetirizine, 60 wt % glyceryl mono-, di- and tri- behenates (COMPRITOL 888) as a matrix material, 15 wt % of the swelling agent croscarmellose sodium (AC-DI-SOL), and 5 wt % of the dissolution enhancer poloxamer 407 (PLURONIC F127) using the following procedure. (Unless otherwise noted, as used in the examples weight percent of materials present in the core refers to weight percent of the uncoated multiparticulate core.) First, 750 g of the COMPRITOL and 62.5 g of the PLURONIC were added to a sealed, jacketed stainless steel tank. Heating fluid at 90° C. was circulated through the jacket of the tank. After about 40 minutes, the mixture had melted, having a temperature of about 90° C. The mixture was then mixed at 75 rpm for 5 minutes. Next, 250 g of cetirizine and 187.5 g of the AC-DI-SOL were added to the melt, mixed by hand, then homogenized for 5 minutes with an overhead homogenizer, resulting in a suspension of the cetirizine and the AC-DI-SOL in the molten components to form a feed.

The so-formed feed was then dispensed at a rate of 145 g/min by pressurizing the tank's headspace with nitrogen at 15 psi to the center of a 4-inch diameter spinning-disk atomizer rotating at 5500 rpm, the surface of which was heated to 90° C. The particles formed by the spinning-disk atomizer were congealed in ambient air and a total of 1100 g of multiparticulates collected.

Samples of the multiparticulate cores were coated with a polymer as follows. A spray solution was prepared by diluting an aqueous ethylcellulose dispersion, Surelease® E-7-7050 (available from Colorcon as an aqueous emulsion containing 25 wt % solids) to 15 wt % solids in water. The multiparticulates were fluidized in a Glatt GPCG-1 fluidized bed coater equipped with a Würster column set at 15 mm. Fluidizing gas (air) was circulated through the bed at a rate of 1000 to 1150 L/min at an inlet temperature of 58° to 68° C. and a bed temperature of 44° to 47° C. The spray solution was introduced to the bed through a two-fluid nozzle at a rate of 3.8 to 7.4 g/min using air with an atomization pressure of 2.2 bar. The multiparticulates were coated for about 150 minutes, resulting in multiparticulates with an average coating weight of 29 wt %. (Unless otherwise noted, in the examples coating weight refers to weight percent of the uncoated multiparticulates.)

The rate of release of cetirizine from the so-formed multiparticulates was determined using the following procedure. A 65-mg sample of the multiparticulates was placed into a USP Type 2 dissoette flask equipped With Teflon-coated paddles rotating at 50 rpm. The flask contained 900 mL of the simulated mouth buffer noted above, held at 37.0±0.5° C. Four-mL samples were taken from the dissoette flask by a syringe with a 10 μm filter attached. The cannula was removed from the syringe, a 0.45-μm filter was attached, 2 mL of sample were returned to the dissolution flask, and 1 mL of sample was filtered into a High Performance Liquid Chromatography (HPLC) vial. The remaining solution in the syringe was drawn from the filter to pull any multiparticulates away from the filter, and returned to the flask. Samples were collected at 1, 2, 3, 5, 10, 20, 30, and 60 minutes following addition of the multiparticulates to the flask. The samples were analyzed using HPLC with a Hewlett Packard 1100 Mac Mod Analytical Zorbax Stablebond CN (SB-CN) column, 5 μm particles, 15 cm×4.6 mm i.d.; mobile phase 100 mM $KH_2PO_4$, pH 6.5/MeOH (50/50) with 1 g/L sodium octanesulfonate at 1.0 mL/min. Absorbance was measured at 214 nm with a diode array spectrophotometer.

The amount of drug released was calculated based on the potency assay of the formulation. To measure the potency of the multiparticulates, about 60 mg (sufficient to obtain a concentration of about 0.1 mg/mL of drug in solution) was weighed and added to a 100 mL volumetric flask. Next, 10 mL acetonitrile was added, and the solution was sonciated for 10 minutes. The flask was filled with the above HPLC mobile phase, and again sonicated for 10 minutes. The solution was filtered and analyzed to determine the total amount of drug in the formulation. The potency assay of the formulation was used to calculate the amount of drug added for each dissolution test. The amount of drug in each sample was divided by the total amount of drug added for the test, and the results are reported as percent of assay. The results of these dissolution tests are given in Table 1.

TABLE 1

| Time (min) | Cetirizine released (%) |
|---|---|
| 0 | 0 |
| 1 | 0 |
| 2 | 1 |
| 3 | 2 |
| 5 | 6 |
| 10 | 35 |
| 20 | 69 |
| 30 | 79 |
| 60 | 85 |

The coated multiparticulates exhibited the desired release profile, with only 6% of the drug released in 5 minutes, followed by rapid and substantially complete release of the drug within one hour.

A panel of five human volunteers was selected to test both the "mouth feel" and the effectiveness of the taste-masking for the so-prepared multiparticulates. Each subject was given 65 mg doses of the multiparticulates, each roughly equivalent to 10mg of active cetirizine. One dose was taken plain and held in the mouth until a bitter taste was experienced. The other dose was taken with a swallow of water and swished around in the mouth until a bitter taste was experienced. The five subjects were also asked to rate the "mouth feel" of the doses by the degree of grittiness felt in the mouth and on the tongue. The reported lag times to the inception of a bitter taste for the multiparticulates taken without water was 2 to 3 minutes, while those for the multiparticulates taken with water was about 30 seconds. All rated the degree of grittiness as very low.

EXAMPLE 2

Example 1 was substantially repeated, with the exceptions that the molten feed was fed to the atomizer at 120 g/min and the rotational speed was 6000 rpm. A photomicrograph of the resulting multiparticulates is shown in FIG. 3. The photomicrograph shows that the process produced small, spherical, and smooth multiparticulate cores.

EXAMPLES 3-5

This example demonstrates applicability of the invention to several drugs. Coated multiparticulates were prepared in substantially the same manner as in Example 1 for the drugs cetirizine (Example 3), azithromycin (Example 4) and caffeine (Example 5), except the coatings comprised 23 wt % and 28 wt % for the cetirizine- and caffeine-loaded cores, respectively. The multiparticulates were formed as follows: 900 g of COMPRITOL and 75 g of PLURONIC were homogenized and heated in a tank equipped with counter-rotating paddles and a homogenizer; and 300 g of drug and 225 g AC-DI-SOL were added to form the molten feed, which was pumped to the atomizer at 140 g/min by a gear pump. The rate of drug release for Example 3 (cetirizine) was measured as in Example 1.

For Example 4 (azithromycin), the drug release rate was measured by prewetting 65 mg of the multiparticulates with 10 mL of dissolution media comprising 0.01 N HCl at pH 2.0, then placing the multiparticulates into a USP Type 2 dissoette flask equipped with TEFLON®-coated paddles rotating at 50 rpm and containing 900 mL of the dissolution media held at 37° C.±0.5° C. A 3-mL sample of the fluid in the flask was then collected at 1, 2, 3, 5, 10, 15, 30, and 60 minutes following addition of the multiparticulates to the flask. The samples were filtered using a 0.45-μm syringe filter prior to analyzing via HPLC (Hewlett Packard 1100, Waters Symmetry $C_8$ column, 45:30:25 acetonitrile:methanol:25 mM $KH_2PO_4$ buffer at 1.0 mL/min, absorbance measured at 210 nm with a diode array spectrophotometer). The amount of drug released was measured as in Example 1.

The rate of release of caffeine from the multiparticulates of Example 5 was measured as in Example 1, except the HPLC analysis was conducted with a Phenomenex Luna C18 column, 5 μm particles, 15 cm±4.6 mm i.d.; mobile phase water/MeOH/acetic acid (69/28/3) at 1.5 mL/min. Absorbance was measured at 275 nm with a diode array spectrophotometer. The amount of drug released was measured as in Example 1.

Figure 4:
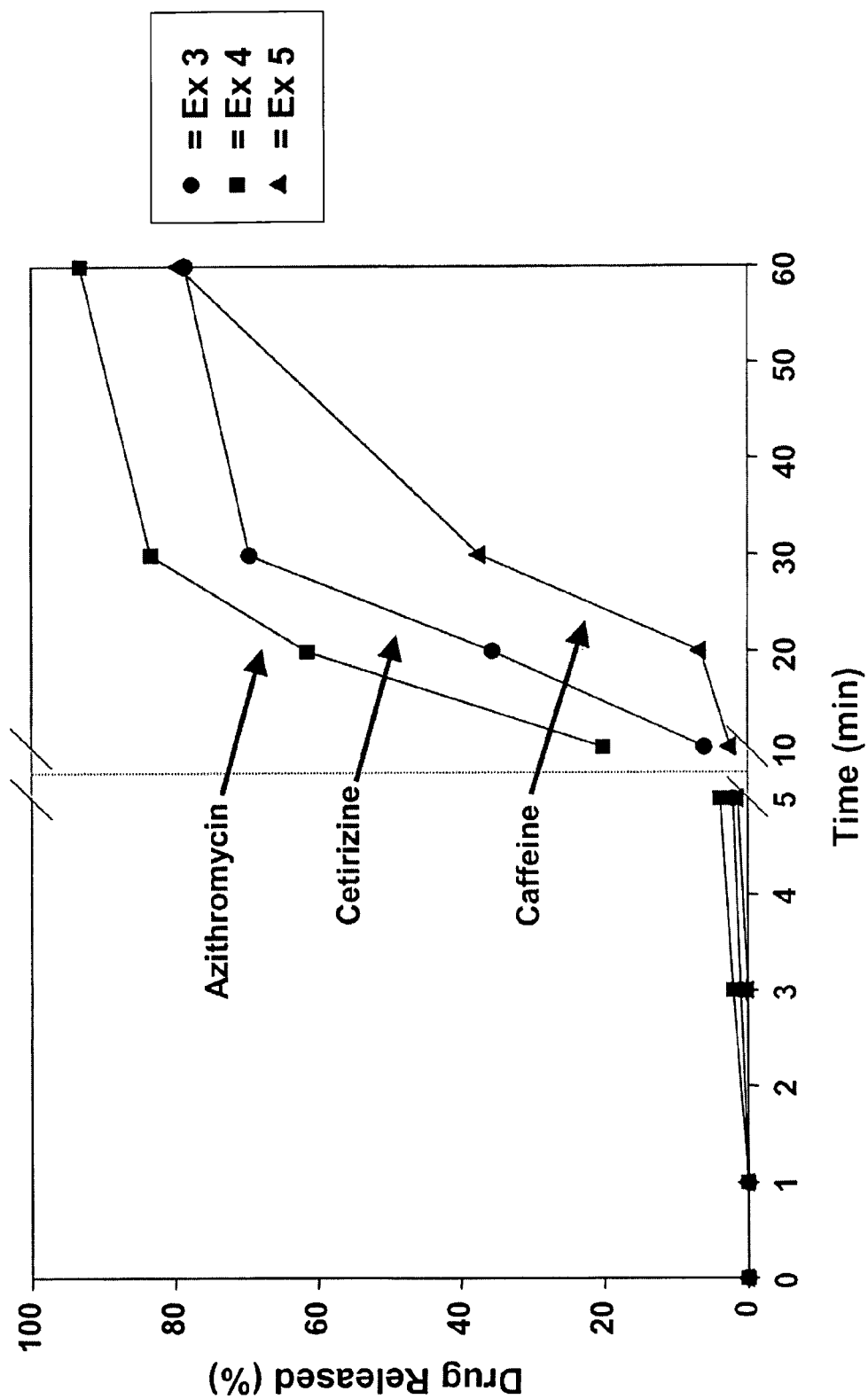
FIG. 4 is a graph showing rate of release of various active agents from the multiparticulates of the invention.

The results of the above dissolution tests are reported in Table 2 and graphically shown in FIG. 4.

TABLE 2

| Ex. No. | Time (min) | Release (%) |
|---|---|---|
| 3 | 0 | 0 |
|   | 1 | 2 |
|   | 2 | 5 |
|   | 3 | 7 |
|   | 5 | 13 |
|   | 10 | 27 |
|   | 10 | 54 |
|   | 30 | 73 |
|   | 60 | 86 |
| 4 | 0 | 0 |
|   | 1 | 0 |
|   | 2 | 2 |
|   | 3 | 4 |
|   | 5 | 20 |
|   | 10 | 61 |
|   | 20 | 83 |
|   | 30 | 93 |
|   | 60 | 102 |
| 5 | 0 | 0 |

TABLE 2-continued

| Ex. No. | Time (min) | Release (%) |
|---|---|---|
|  | 1 | 0 |
|  | 2 | 0 |
|  | 3 | 1 |
|  | 5 | 2 |
|  | 10 | 7 |
|  | 20 | 37 |
|  | 30 | 79 |
|  | 60 | 100 |

EXAMPLE 6

The example demonstrates multiparticulates having a small mean diameter. Cetirizine-containing coated multiparticulates were prepared as in Example 3 with the following differences: drug comprised 15 wt%; the COMPRITOL was 55 wt %; the LUTROL was 15 wt %; the swelling agent was sodium starch glycolate (EXPLOTAB) and was 15 wt %; and the disk speed was 10,000 rpm. The coating was present in an amount of 49 wt % and the volume-weighted mean diameter of the uncoated multiparticulates was calculated at 80 μm by measuring the mean diameter by laser light scattering using a Malvern Mastersizer 2000 using the dry powder feed method and taking samples with a dispersive air pressure of 3.45 bar, a vibration feed rate of 50-75% of maximum, and at a rate of 3 measurements per aliquot with a delay time of 7 seconds. Volume-weighted mean diameter was calculated assuming a gaussian size distribution, with approximately 85% of the particle volume being within about 30% of the reported size. The rate of drug release for the so-prepared multiparticulates was measured as in Example 1 and the results are reported in Table 3.

TABLE 3

| Time (min) | Release (%) |
|---|---|
| 0 | 0 |
| 1 | 0 |
| 2 | 0 |
| 3 | 0 |
| 5 | 3 |
| 10 | 13 |
| 20 | 31 |
| 30 | 45 |
| 60 | 80 |

EXAMPLE 7

Figure 5:
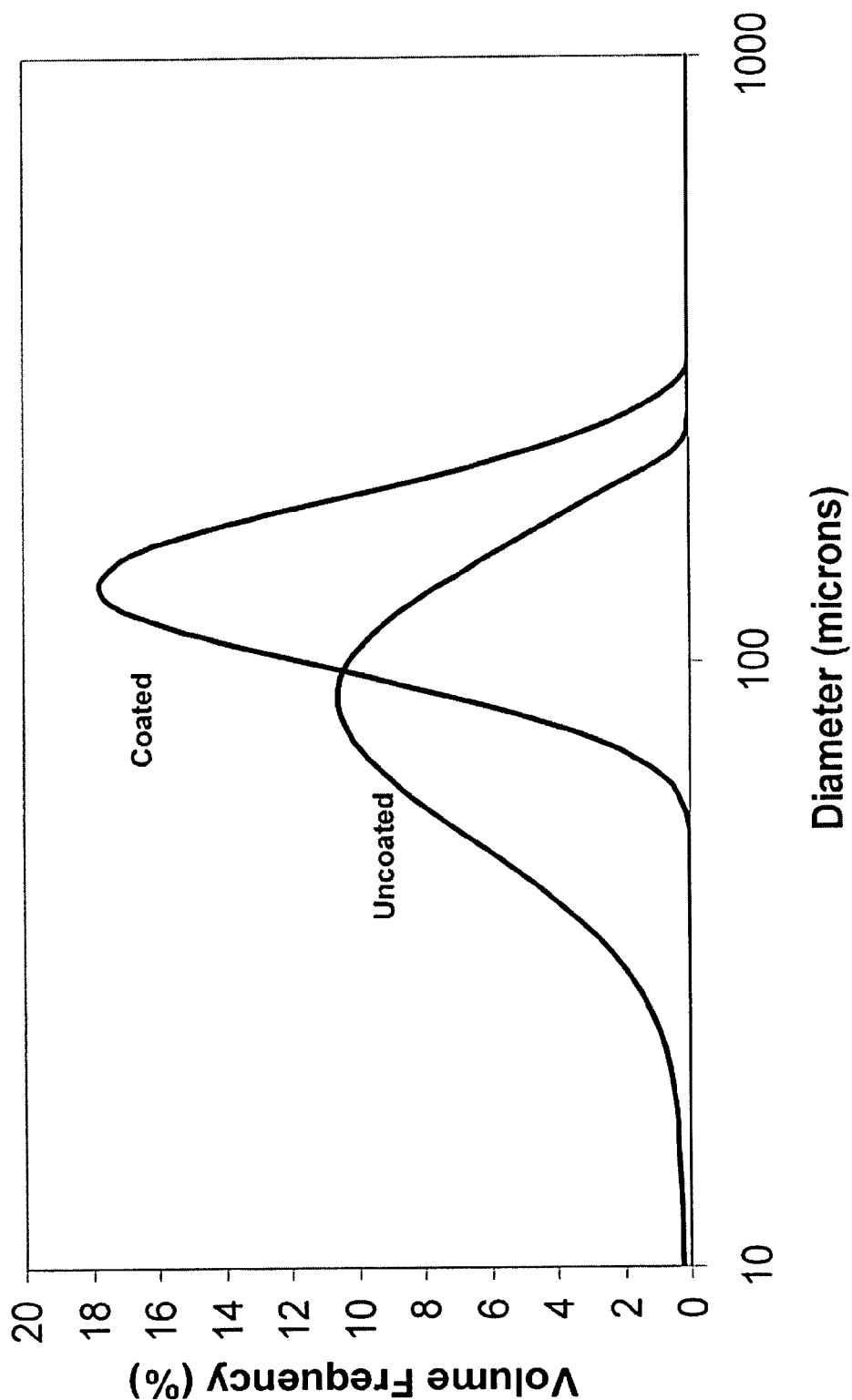
FIG. 5 is a graph showing particle size distribution of exemplary multiparticulates of the invention.

This example demonstrates multiparticulates having a small mean diameter. Example 6 was substantially repeated, except the coating was present in an amount of 46 wt %. The volume-weighted mean diameter of the uncoated and coated cores was measured as in Example 6 and determined to be 85 and 135 microns, respectively. A plot of the diameter of these multiparticulates vs. % volume frequency is shown in FIG. 5.

EXAMPLES 8-10

Figure 6:
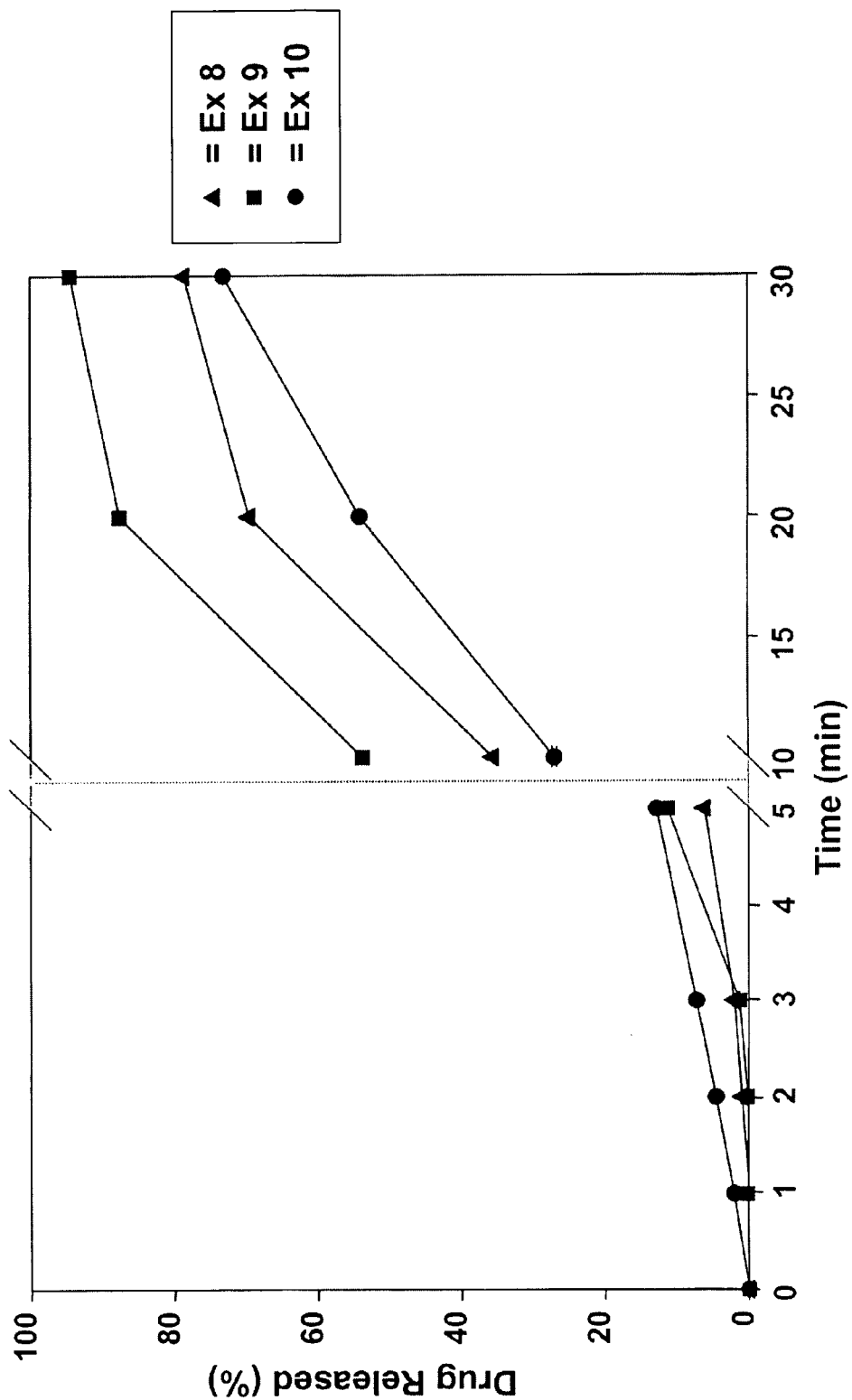
FIG. 6 is a graph showing the rate of release of the drug cetirizine from the multiparticulates of the invention using various coatings.

This example demonstrates the use of several coatings. Cetirizine-loaded coated multiparticulates were prepared as in Example 1, except that the coatings were varied and contained various plasticizers as follows: Example 8—ethyl cellulose coating containing coconut oil as plasticizer (Surelease® E-7-19010, available from Colorcon, West Point, Pa., as an aqueous emulsion containing 25 wt % solids diluted to 15 wt % solids using deionized water) (coating 28 wt %); Example 9—ethyl cellulose coating containing dibutyl sebacate as plasticizer (Surelease® E-7-7050, available from Colorcon as an aqueous emulsion containing 25 wt % solids diluted to 15 wt % solids using deionized water) (coating 26 wt %); and Example 10—EUDRAGIT RS containing triethyl citrate (the coating solution consisted of 8 wt % Eudragit® RS, available from Rohm America, Piscataway, N.J., 0.8 wt % triethyl citrate, 45.6 wt % acetone, 5.0 wt % talc, and 45.6 wt % IPA) (coating 23 wt %). The rate of drug release was measured as in Example 1 and the results are reported in Table 4 and shown graphically in FIG. 6.

Control 1 was prepared as in Example 1 except that the coating was cellulose acetate containing polyethylene glycol (the coating solution consisted of 9.75 wt % cellulose acetate CA 398-10 available from Eastman, 0.25 wt % PEG 3350, 6.0 wt % water and 84.0 wt % acetone) (coating 28 wt %).

TABLE 4

| Ex. No. | Time (min) | Release (%) |
|---|---|---|
| 8 | 0 | 0 |
|  | 1 | 1 |
|  | 2 | 4 |
|  | 3 | 9 |
|  | 5 | 28 |
|  | 10 | 62 |
|  | 20 | 87 |
|  | 30 | 92 |
|  | 60 | 98 |
| 9 | 0 | 0 |
|  | 1 | 0 |
|  | 2 | 3 |
|  | 3 | 22 |
|  | 5 | 66 |
|  | 10 | 89 |
|  | 20 | 96 |
|  | 30 | 98 |
|  | 60 | 98 |
| 10 | 0 | 0 |
|  | 1 | 2 |
|  | 2 | 5 |
|  | 3 | 7 |
|  | 5 | 13 |
|  | 10 | 27 |
|  | 20 | 54 |
|  | 30 | 73 |
|  | 60 | 86 |
| Control 1 | 0 | 0 |
|  | 1 | 0 |
|  | 2 | 1 |
|  | 3 | 2 |
|  | 5 | 3 |
|  | 10 | 6 |
|  | 20 | 9 |
|  | 30 | 10 |
|  | 60 | 10 |

The results in Table 4 show that the coating must be relatively weak so as to be ruptured by the swelling agent. Control 1 shows that a 28 wt % cellulose acetate coating for these cores was too strong to allow rupture to occur sufficiently fast, presumably due to a higher tensile strength relative to the other coatings. In contrast, both ethyl cellulose and the polymethacylate EUDRAGIT RS coatings provided a short delay followed by substantially complete release in one hour.

EXAMPLES 11-12

Figure 7:
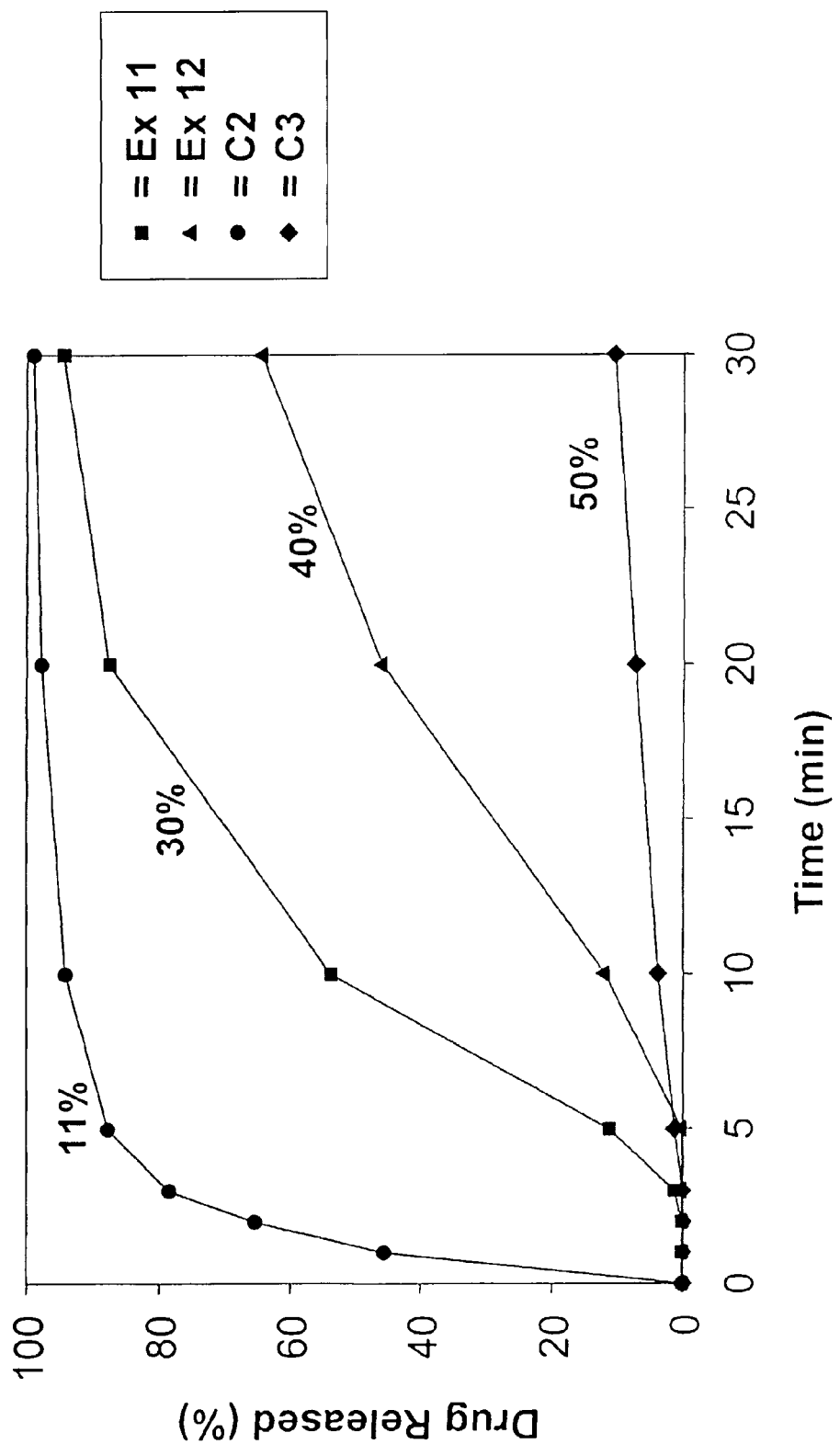
FIG. 7 is a graph showing the rate of release of the drug cetirizine from the multiparticulates of the invention using various coating thicknesses.

This example shows that the coating weight should be selected so as to achieve the desired release rate. Cetirizine-loaded coated multiparticulates were prepared as in Example 1, except the amount of coating was varied as follows: Example 11-30 wt %; Example 12-40 wt %. The rate of drug release was measured as in Example 1, and the results are reported in Table 5 and shown graphically in FIG. 7.

Controls 2 and 3

Controls 2 and 3 were prepared as in Example 11 except that for Control 2 the coating was 11 wt %, and for Control 3 the coating was 50 wt %.

TABLE 5

| Ex. No. | Time (min) | Release (%) |
|---|---|---|
| 11 | 0 | 0 |
|  | 1 | 0 |
|  | 2 | 0 |
|  | 3 | 1 |
|  | 5 | 11 |
|  | 10 | 54 |
|  | 20 | 88 |
|  | 30 | 94 |
|  | 60 | 100 |
| 12 | 0 | 0 |
|  | 1 | 0 |
|  | 2 | 0 |
|  | 3 | 0 |
|  | 5 | 0 |
|  | 10 | 12 |
|  | 20 | 46 |
|  | 30 | 64 |
|  | 60 | 79 |
| C2 | 0 | 0 |
|  | 1 | 45 |
|  | 2 | 65 |
|  | 3 | 78 |
|  | 5 | 88 |
|  | 10 | 94 |
|  | 20 | 98 |
|  | 30 | 99 |
|  | 60 | 98 |
| C3 | 0 | 0 |
|  | 1 | 0 |
|  | 2 | 0 |
|  | 3 | 0 |
|  | 5 | 1 |
|  | 10 | 4 |
|  | 20 | 7 |
|  | 30 | 10 |
|  | 60 | 26 |

As the data show, Examples 11 and 12 provide an initially delayed release, followed by substantially complete release in one hour. However, Control 2, having a thin coating, released too quickly, whereas Control C3, having a thick coating, did not release quickly enough.

EXAMPLES 13 AND 14

This example shows multiparticulates formed having a small size. Cetirizine-containing coated multiparticulates were prepared as in Example 6 with the following differences: the drug loading was 15 wt %; the matrix material was hydrogenated cottonseed oil (LUBRITAB) at 60 wt %; and the swelling agent, sodium starch glycolate (EXPLOTAB), was present at 25 wt %. The mean diameter of the uncoated cores was measured as described in Example 6 and determined to be 76 microns. The coating was 55 wt % EUDRAGIT NE30D and 45 wt % talc. The coating was present in the amount of 27.8 wt % for Example 13 and 38.5% for Example 14. The rate of drug release for the so-prepared multiparticulates was measured as in Example 1 and the results are reported in Table 6.

TABLE 6

| Ex. No. | Time (min) | Release (%) |
|---|---|---|
| 13 | 0 | 0 |
|  | 1 | 0 |
|  | 2 | 4 |
|  | 3 | 8 |
|  | 5 | 13 |
|  | 10 | 28 |
|  | 20 | 53 |
|  | 30 | 67 |
|  | 60 | 82 |
| 14 | 0 | 0 |
|  | 1 | 0 |
|  | 2 | 0 |
|  | 3 | 0 |
|  | 5 | 10 |
|  | 10 | 20 |
|  | 20 | 42 |
|  | 30 | 58 |
|  | 60 | 80 |

The results show the small multiparticulates provided a short delay before releasing greater than 80 wt % of the drug within sixty minutes following administration to the use environment.

EXAMPLES 15 AND 16

The example demonstrates incorporation of the multiparticulates into a chewable tablet. The cetirizine-containing coated multiparticulates of Examples 11 and 12 were incorporated into chewable tablets to form Examples 15 and 16. The chewable tablets of Example 15 contained 8.1 wt % of the multiparticulates of Example 11, 91.4 wt % confectioners sugar, and 0.5 wt % magnesium stearate. The tablets of Example 16 contained 8.7 wt % of the multiparticulates of Example 12, 90.8 wt % confectioners sugar, and 0.5 wt % magnesium stearate. To form the tablets, the multiparticulates and the sugar were combined and mixed in a Turbula blender for 20 minutes. Next, the magnesium stearate was added and blended for 4 minutes. The mixture was then weighed into 800 mg samples and formed into tablets on an F-Press using ½" flat, beveled (FB) tooling. The compression force was set to deliver tablets with a hardness of 5 kiloponds (kP) (Example 15) or 2 kP (Example 16).

A panel of five human volunteers was selected to test the effectiveness of the taste-masking for the so-prepared chewable tablets. Each subject was given a tablet containing 65 mg of the multiparticulates, which contained about 10 mg of active cetirizine. The tablet was taken with a swallow of water and swished around in the mouth until a bitter taste was experienced. The reported lag times to the inception of a bitter taste was about 30 to 45 seconds.

EXAMPLE 17

The example demonstrates another chewable tablet. The cetirizine-containing coated multiparticulates of Example 14 were incorporated into chewable tablets to form Example 17. The chewable tablets contained 14.9 wt % of the multiparticulates of Example 14, 15.0 wt % and 10.0 wt % of two grades of microcrystalline cellulose (Avicel PH200 and Avicel CE1 5, respectively from FMC Corporation of Philadelphia, Pa.,) 58.4 wt % processed sucrose (commercially available as DiPac from Domino Sugar), 1.3 wt % croscarmellose sodium (commercially available as AcDiSol from FMC Corporation), and 0.5 wt % magnesium stearate. To form the tablets, all ingredients except magnesium stearate were combined and blended using the Turbula mixer, then the magnesium stearate was added and blended. The mixture was then formed into tablets on an F-Press using ½" flat, beveled (FB) tooling. The compression force was set to deliver tablets with a hardness of 5 kiloponds (kP).

A panel of four human volunteers was selected to test the effectiveness of the taste-masking for the so-prepared chewable tablets. Each subject was given a tablet containing about 10 mg of active cetirizine. Tablets were chewed and held in the mouth for about 2 minutes. Very slight to no bitterness was reported by all four tasters for 1.5 to 2 minutes, when the material was removed from the mouth.

EXAMPLE 18

Multiparticulate cores comprising 5 wt % valdecoxib, 55 wt % COMPRITOL 888, 35.0 wt % croscarmellose sodium (AC-DI-SOL), and 5 wt % of a mixture of fatty acid esters of glycerol and polyethylene glycol (commercially available as GELUCIRE 50/13 from Gattefossé Corporation) were prepared using the following procedure. The AC-DI-SOL was ball-milled to reduce the particle size. The COMPRITOL 888 and the GELUCIRE 50/13 were added to a sealed, jacketed stainless-steel 1 L tank equipped with a mechanical mixing paddle. Heating fluid was circulated through the jacket of the tank. After about 120 minutes, the mixture had melted, having a temperature of about 93° C. The AC-DI-SOL and valdecoxib were added to the melt and homogenized at 5000 rpm for 5 minutes, resulting in a molten feed. The molten feed was pumped at a rate of 110 g/min using a gear pump (Zenith Pump, Parker Hannifin Corp, Model C-9000, 2.4 cc/rev) to the center of a 4-inch diameter spinning-disk atomizer. The surface of the spinning disk atomizer was maintained at 90° C. and the disk was rotated at 10,000 rpm while forming the multiparticulates. The particles formed by the spinning-disk atomizer were congealed in ambient air and collected. Table 7 summarizes the processing variables.

TABLE 7

| Multiparticulates | Formulation (wt/wt) | Feed Rate (g/min) | Disk speed (rpm) | Disk Temp (° C.) | Batch size (g) |
|---|---|---|---|---|---|
| Example 18 | Valdecoxib/ COMPRITOL 888/ AC-DI-SOL/ GELUCIRE 50/13 5/55/35/5 | 110 | 10,000 | 90 | 286 |
| Example 19 | Valdecoxib/ COMPRITOL 888/ AC-DI-SOL/ GELUCIRE 50/13 10/50/35/5 | 75 | 10,000 | 86 | 25 |
| Example 20 | Valdecoxib/ COMPRITOL 888/ AC-DI-SOL/ GELUCIRE 50/13 10/45/35/10 | 75 | 10,000 | 88 | 20 |
| Example 21 | Valdecoxib/ COMPRITOL 888/ AC-DI-SOL/ GELUCIRE 50/13 10/60/20/10 | 110 | 5500 | 90 | 985 |

The rate of release of valdecoxib in vitro from multiparticulate cores of Example 18 was determined using the following procedure. About 28 mg of the multiparticulates of Example 18 were placed into a USP Type 2 dissoette flask equipped with Teflon-coated paddles rotating at 100 rpm. The flask contained 900 mL of simulated mouth buffer ($KH_2PO_4$ buffer, pH 7.3, with 0.5 wt % polysorbate 80 (sold as Tween™ 80, available commercially from ICI)) at 37.0±0.5° C. Samples were taken using a syringe attached to a cannula with a 70 μm filter. A sample of the fluid in the flask was drawn into the syringe, the cannula was removed, and a 0.45-μm filter was attached to the syringe.

One mL of sample was filtered into a High Performance Liquid Chromatography (HPLC) vial. Samples were collected at 0, 1, 2, 3, 5, 10, 20, 30, and 60 minutes following addition of the multiparticulates to the flask. The samples were analyzed using HPLC (Zorbax SB-C8 column, 3.5 μm particles, 7.5 cm×4.6 mm i.d.; 55/45 5 mM triethanolamine, pH 7.0/acetonitrile at 1.5 mL/min; absorbance measured at 256 nm with a diode array spectrophotometer).

The amount of drug released was calculated based on the potency assay of the formulation. To measure the potency of the multiparticulates of Example 18, about 80 mg of the multiparticulates were weighed and added to a 25 mL volumetric flask. Next, about 10 mL acetonitrile/methanol (80/20 vol/vol) was added, and the solution was sonicated for 15 minutes. The flask was cooled to room temperature and filled to volume with acetonitrile/methanol (80/20 vol/vol). An aliquot of the solution was then centrifuged for 5 minutes at 13,000 rpm, and analyzed to determine the total amount of drug in the formulation. The potency assay of the formulation was used to calculate the amount of drug added for each dissolution test. The amount of drug in each sample was divided by the total amount of drug added for the test, and the results are reported as percent of assay. The results of these dissolution tests are given in Table 8.

TABLE 8

| Time (min) | Valdecoxib Released from multiparticulates of Example 18 (% assay) |
|---|---|
| 0 | 0 |
| 1 | 26 |
| 2 | 38 |
| 3 | 45 |
| 5 | 54 |
| 10 | 69 |
| 20 | 83 |
| 30 | 88 |
| 60 | 98 |

The results in Table 8 show rapid and complete release of valdecoxib from the multiparticulates.

EXAMPLES 19-21

The multiparticulate cores of Example 19 were made comprising 10 wt % valdecoxib, 50 wt % COMPRITOL 888, 35.0 wt % AC-DI-SOL, and 5 wt % GELUCIRE 50/13. The AC-DI-SOL was ball-milled to reduce the particle size. First, the COMPRITOL and GELUCIRE 50/13 were added to a beaker and heated in an oven to form a melt (approximately 20 minutes), with a temperature of about 90° C. Next, AC-DI-SOL and valdecoxib were added to the melt and stirred at 700 rpm for 5 minutes, resulting in a molten feed.

The molten feed was then pumped, using a jacketed syringe controlled by a linear actuator, to the center of a 4-inch diameter spinning-disk atomizer, the surface of which was heated to 86° C. The disk was spinning at 10,000 rpm. The particles formed by the spinning-disk atomizer were congealed in ambient air and collected. Table 7 summarizes the processing variables.

The multiparticulate cores of Examples 20-21 were made in a similar fashion using the compositions and processes given in Table 7, except that for Example 21 the AC-DI-SOL was milled to reduce the particle size to an average of about 10 microns.

The rate of release of valdecoxib in vitro from multiparticulate cores of Examples 19-21 was determined using the procedure described above. Results are shown in Table 9.

TABLE 9

| Example No. | Time (min) | Valdecoxib Released (% assay) |
|---|---|---|
| 19 | 0 | 0 |
|  | 1 | 27 |
|  | 2 | 37 |
|  | 3 | 44 |
|  | 5 | 53 |
|  | 10 | 66 |
|  | 20 | 79 |
|  | 30 | 86 |
|  | 60 | 98 |
| 20 | 0 | 0 |
|  | 1 | 24 |
|  | 2 | 32 |
|  | 3 | 38 |
|  | 5 | 47 |
|  | 10 | 60 |
|  | 20 | 73 |
|  | 30 | 79 |
|  | 60 | 84 |
| 21 | 0 | 0 |
|  | 1 | 14 |
|  | 2 | 21 |
|  | 3 | 27 |
|  | 5 | 34 |
|  | 10 | 48 |
|  | 20 | 64 |
|  | 30 | 75 |
|  | 60 | 93 |

The results in Table 9 show valdecoxib released from multiparticulates comprising valdecoxib, COMPRITOL, AC-DI-SOL, and GELUCIRE 50/13 in varying ratios.

EXAMPLE 22

The multiparticulate cores of Example 19 were coated with an anti-enteric polymer as follows. The coating solution contained 42.4 g (8 wt %) of a cationic copolymer based on dimethylaminoethyl methacrylate and neutral methacrylates (EUDRAGIT® E PO, Rohm America, Inc. Pascataway, N.J.), 291.3 g (55 wt %) isopropyl alcohol, and 196.0 g (37 wt %) acetone. The solution was sprayed onto 80 g of the melt-congeal cores in a Mini-Glatt fluid bed coater with a Würster column. The spray solution was pumped into the fluid bed coater at a rate of 2.7 g/min. The inlet temperature was 33° C., atomizing air pressure was 2.2 barg, and fluidizing gas flow rate was 22 ft³/min. After 33 wt % coating had been added (coating/core), the spray solution flow was discontinued, and the coated multiparticulates were dried for 5 minutes with the fluidizing gas.

The rate of release of valdecoxib in vitro from multiparticulates of Example 22 was determined using the following procedure. About 244 mg of the multiparticulates were placed into a USP Type 2 dissoette flask equipped with Teflon-coated paddles rotating at 100 rpm. The flask initially contained 300 mL of simulated gastric buffer (0.01 M HCl, pH 2.0, 0.7 wt % NaCl, and 0.5 wt % polysorbate 80 (sold as Tween™ 80, available commercially from ICI)), at 37.0±0.5° C. After 30 minutes, 600 mL of 50 mM $KH_2PO_4$ buffer, at pH 7.3, with 0.5 wt % Tween™ 80 was added to the dissoette flask. The final pH of the test solution was about 7.2. Samples were taken using a syringe attached to a cannular with a 70 μm filter. A sample of the fluid in the flask was drawn into the syringe, the cannula was removed, and a 0.45-μm filter was attached to the syringe. One mL of sample was filtered into a High Performance Liquid Chromatography (HPLC) vial. Samples were collected at the times shown in Table 2. The samples were analyzed using HPLC (Zorbax SB-CB column, 3.5 μm particles, 7.5 cm×4.6 mm i.d.; 55/45 5 mM triethanolamine, pH 7.0/acetonitrile at 1.5 mL/min; absorbance measured at 256 nm with a diode array spectrophotometer).

The amount of drug released was calculated based on the potency assay of the formulation. The results of these dissolution tests are given in Table 10 and show substantially all of the drug was released from the multiparticulates.

TABLE 10

| Example No. | Time (min) | Valdecoxib Released (% assay) |
|---|---|---|
| 22 | 0 | 0 |
|  | 5 | 37 |
|  | 29 | 72 |
|  | 31 | 80 |
|  | 32 | 75 |
|  | 33 | 75 |
|  | 35 | 76 |
|  | 40 | 79 |
|  | 50 | 84 |
|  | 60 | 88 |
|  | 95 | 94 |
|  | 120 | 95 |

EXAMPLE 23

The multiparticulates of Example 21 were coated with an anti-enteric coating as described in Example 22, except that the coating amount to 59 wt % (coating/core).

The rate of release of valdecoxib was determined in vitro using by measuring drug release in separate flasks containing gastric buffer or simulated mouth buffer, and the graphs were combined to approximate a mouth buffer/ gastric fluid transfer test (transfer from mouth buffer after 5 minutes). The results of this test, summarized in Table 11, show that after an initial lag time, the multiparticulates rapidly released valdecoxib.

TABLE 11

| Example No. | Time (min) | Valdecoxib Released (% assay) |
|---|---|---|
| 23 | 0 | 0 |
|  | 1 | 0 |
|  | 2 | 0 |
|  | 3 | 0 |
|  | 5 | 1 |
|  | 10 | 26 |
|  | 20 | 38 |
|  | 30 | 47 |
|  | 60 | 65 |

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

The invention claimed is:

1. A pharmaceutical composition comprising a plurality of multiparticulates, each of said multiparticulates comprising:
   (a) a core comprising a drug, said core being surrounded by a coating selected from the group consisting of (i) a water-permeable, substantially drug impermeable coating and (ii) an anti-enteric coating;
   (b) said core further comprising a dissolution enhancer and a matrix material that is solid at 25° C. and having a melting point lower than the melting point of said drug and being present in an amount of at least 30 wt % of said core and wherein said matrix material is selected from the group consisting of alkyl-containing glycerols, hydrogenated cottonseed oil, and mixtures thereof;
   (c) said core further comprising a water-swellable swelling agent, said water-swellable swelling agent being capable of imbibing fluid and swelling so as to rupture said coating or disintegrate said core, thereby releasing said drug.

2. A pharmaceutical composition comprising a plurality of multiparticulates, each of said multiparticulates comprising
   (a) a core comprising a drug, said core being surrounded by a coating selected from the group consisting of (i) a water-permeable, substantially drug impermeable coating and (ii) an anti-enteric coating; and,
   (b) said core comprising a matrix material that is solid at 25° C. and having a melting point lower than the melting point of said drug and being present in an amount of at least 30 wt % of said core and wherein said matrix material is selected from the group consisting of alkyl-containing glycerols, hydrogenated cottonseed oil, and mixtures thereof;
   (c) said multiparticulates have a volume-weighted mean diameter after coating of less than 150 μm; and
   (d) said core further comprising a dissolution enhancer and a water-swellable swelling agent present in an amount of from 5 wt % to 30 wt % of said core, wherein said water-swellable swelling agent is capable of imbibing fluid and swelling so as to rupture said coating or disintegrate said core, thereby releasing said drug.

3. The composition of claim 1 or 2 wherein said water-swellable swelling agent is capable of increasing in volume by a factor of at least 2 within one hour in an in vitro simulated gastric use environment consisting of 0.01 M HCl and 0.12 M NaCl in deionized water.

4. The composition of claim 1 or 2 wherein said swelling agent is selected from the group consisting of croscarmellose sodium, sodium starch glycolate, and crospovidone.

5. The composition of claim 1 or 2 wherein said coating is selected from the group consisting of ethyl cellulose, methyl cellulose, hydroxyethyl cellulose, hydroxypropyl cellulose, and hydroxypropylmethyl cellulose, polymethacrylates, polyethylene glycol, polyethylene oxide, polypropylene glycol, polyethylene-polypropylene glycol copolymers, polyvinyl pyrrolidinone, starch, dextran, dextrin, polydextrose, polyalkenes, polyethers, polysulfones, polyethersulfones, polystyrenes, polyvinyl alcohol, polyvinyl halides, polyvinyl ethers, paraffin wax, microcrystalline wax, and synthetic wax.

6. The composition of claim 1 or 2 wherein said coating comprises a polymer selected from the group consisting of ethyl cellulose and polymethacrylate.

7. The composition of claim 1 or 2 wherein said coating is an antienteric coating and comprises a material selected from the group consisting of butyl methacrylate/(2-dimethylaminoethyl)methacrylate/methyl methacrylate copolymer and polyvinylacetal diethylaminoacetate.

8. The composition of claim 7 wherein said coating comprises a butyl methacrylate/(2-dimethylaminoethyl)methacrylate/methyl methacrylate copolymer.

9. The composition of claim 1 or 2 wherein said drug and said swelling agent are encapsulated within said matrix.

10. The composition of claim 1 or 2 wherein said matrix material is selected from the group consisting of glyceryl monooleate, glyceryl monostearate, glyceryl palmitostearate, mono-, di-, and trialkyl glycerides, glyceryl monobehenate, glyceryl dibehenate, glyceryl tribehenate, glyceryl tristearate, glyceryl tripalmitate, and mixtures thereof.

11. The composition of claim 1 wherein said multiparticulates have a volume-weighted mean diameter after coating of less than 150 μm.

12. The composition of claim 1 or 2 incorporated into a compressed dosage form.

13. The composition of claim 1 or 2 wherein said drug is selected from the group consisting of cetirizine, azithromycin, eletriptan, valdecoxib and caffeine.

14. The composition of claim 1 or 2 wherein said drug is a low solubility drug having an aqueous solubility at pH 1-8 of 1 mg/mL or less.

* * * * *